US007635696B2

(12) United States Patent  
Andrés-Gil et al.

(10) Patent No.: US 7,635,696 B2  
(45) Date of Patent: Dec. 22, 2009

(54) ISOXAZOLINE-INDOLE DERIVATIVES WITH AN IMPROVED ANTIPSYCHOTIC AND ANXIOLYTIC ACTIVITY

(75) Inventors: José Ignacio Andrés-Gil, Madrid (ES); José Manuel Bartolomé-Nebreda, Toledo (ES); Manuel Jesus Alcázar-Vaca, Toledo (ES); Maria de las Mercedes Garcia-Martin, Madrid (ES); Antonius Adrianus Hendrikus Petrus Megens, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/791,510

(22) PCT Filed: Nov. 25, 2005

(86) PCT No.: PCT/EP2005/056229

§ 371 (c)(1),  
(2), (4) Date: May 24, 2007

(87) PCT Pub. No.: WO2006/056600

PCT Pub. Date: Jun. 1, 2006

(65) Prior Publication Data

US 2008/0113988 A1 May 15, 2008

(30) Foreign Application Priority Data

Nov. 26, 2004 (EP) .................................. 04106123

(51) Int. Cl.

| | |
|---|---|
| A61K 31/535 | (2006.01) |
| A61K 31/445 | (2006.01) |
| A61K 31/44 | (2006.01) |
| C07D 261/20 | (2006.01) |
| C07D 413/00 | (2006.01) |

(52) U.S. Cl. .................... 514/235.5; 514/321; 514/338; 546/198; 546/272.1

(58) Field of Classification Search ........................ None  
See application file for complete search history.

(56) References Cited

U.S. PATENT DOCUMENTS

| | | | |
|---|---|---|---|
| 5,965,595 A | 10/1999 | Maurer et al. | |
| 6,313,126 B1 | 11/2001 | Newshaw et al. | |
| 2006/0116378 A1* | 6/2006 | Andres-Gil et al. ......... | 514/248 |

FOREIGN PATENT DOCUMENTS

| | | |
|---|---|---|
| EP | 0 705 600 A1 | 4/1996 |
| EP | 0 943 613 A1 | 9/1999 |
| EP | 1 078 928 A1 | 2/2001 |
| WO | WO 99/55672 A2 | 11/1999 |
| WO | WO 00/40580 A1 | 7/2000 |
| WO | WO 00/40581 A1 | 7/2000 |
| WO | WO 00/64898 A1 | 11/2000 |
| WO | WO 02/40465 A2 | 5/2002 |
| WO | WO 02/48105 A2 | 6/2002 |
| WO | WO 02/066484 A1 | 8/2002 |
| WO | WO 02/085911 A1 | 10/2002 |
| WO | WO 03/002552 A1 | 1/2003 |
| WO | WO 03/002556 A1 | 1/2003 |
| WO | WO 03/010169 A1 | 2/2003 |
| WO | WO 03/082878 A1 | 10/2003 |
| WO | WO 2004/016621 A1 | 2/2004 |
| WO | WO 2004/018482 A2 | 3/2004 |
| WO | WO 2004/018483 A1 | 3/2004 |

OTHER PUBLICATIONS

Kling et al., Bioorg. Med. Chem. Lett, 15(2005), 5567-5573.*  
Shireman et al., Bioorg. Med. Chem. Lett, 18 (2008), 2103-2108.*  
Andres et al., caplus an 2003:535065.*  
Andres, J.I. et al., "Synthesis of 3a,4-Dihydro-3H-[1]Benzopyrano[4,3-c]isoxazoles, Displaying Combined 5-HT Uptake Inhibiting and .Alpha2-Adrenoceptor Antagonistic Activities: A Novel Series of Potential Antidepressants", *Bioorganic & Medicinal Chemistry Letters*, 2003, 13, 2719-2725.  
Stella, V. J. et al., "Prodrugs. Do they have advantages in clinical practice?" *Drugs,* 1985, 29, 455-473.  
Stella, V. J. et al., "Prodrugs", *Drug Delivery Systems,* 1985, pp. 112-176.  
Wilson, C. O. et al., (Ed.), *Textbook of Organic Medicinal and Pharmaceutical Chemistry,* Seventh Edition, 1977, J. B. Lippincott Company, pp. 70-75.

* cited by examiner

*Primary Examiner*—Kamal A Saeed  
*Assistant Examiner*—Sun Jae Y Loewe  
(74) *Attorney, Agent, or Firm*—Woodcock Washburn, LLP

(57) ABSTRACT

The present invention relates to novel isoxazoline-indole derivatives according to Formula (I), a pharmaceutically acceptable acid or base addition salt thereof, a stereochemically isomeric form thereof, an N-oxide form thereof or a quaternary ammonium salt thereof, with a binding affinity towards dopamine receptors, in particular towards dopamine $D_2$ and/or $D_3$ receptors, with selective serotonin reuptake inhibition (SSRI) properties and showing an affinity for the 5-$HT_{1A}$ receptor, pharmaceutical compositions comprising the compounds according to the invention, the use thereof for the prevention and/or treatment of a range of psychiatric and neurological disorders, in particular certain psychotic disorders, most in particular schizophrenia and processes for their production, wherein the variables are further defined in the application.

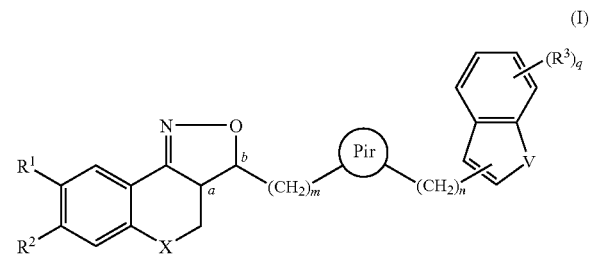

9 Claims, No Drawings

ISOXAZOLINE-INDOLE DERIVATIVES WITH AN IMPROVED ANTIPSYCHOTIC AND ANXIOLYTIC ACTIVITY

CROSS-REFERENCE TO RELATED APPLICATIONS

This application is the U.S. National Stage of International Application No. PCT/EP2005/056229 (International Publication Number WO 2006/056600 A1, published Jun. 1, 2006), filed Nov. 25, 2005, which in turn claims the benefit of priority of European Application EP 04106123.5, filed Nov. 26, 2004, both of which are incorporated herein by reference in their entireties.

FIELD OF THE INVENTION

The present invention relates to novel isoxazoline-indole derivatives with a binding affinity towards dopamine receptors, in particular towards dopamine $D_2$ and/or $D_3$ receptors, with selective serotonin reuptake inhibition (SSRI) properties and showing an affinity for the 5-$HT_{1A}$ receptor, pharmaceutical compositions comprising the compounds according to the invention, the use thereof for the prevention and/or treatment of a range of psychiatric and neurological disorders, in particular certain psychotic disorders, most in particular schizophrenia and processes for their production.

BACKGROUND OF THE INVENTION

As all currently available antipsychotics have central $D_2$ antagonism in common, blockade of central $D_2$ receptors (or neuroleptic activity) is generally considered as a pharmacological prerequisite for antipsychotic activity.

Currently available antipsychotics are indeed highly effective against the positive symptoms of schizophrenia (hallucinations, aggression, excitation) but not or to a lesser extent against the affective, depressive and negative symptoms of the disease (although some progress in this respect has been made with the introduction of serotonine-dopamine antagonists such as clozapine, risperidone, olanzapine, etc.). In common practice, antidepressants (predominantly SSRIs) are often co-administered as add-on therapy to neuroleptic treatment, e.g. the majority of schizophrenic patients is treated both with antipsychotics (central $D_2$-antagonists) as well as with antidepressants, predominantly selective serotonin (5-HT) reuptake inhibitors (SSRIs) (see e.g. EP 830 864 A1 by Eli Lilly). SSRIs are a well-known class of antidepressants and useful for the treatment of panic disorders and social phobia.

Furthermore, clinical and pharmacological studies have shown that compounds that show additional 5-$HT_{1A}$ antagonism also show an improved onset of action and are useful in the treatment of a range of affective disorders such as generalised anxiety disorder, panic disorder, obsessive compulsive disorder, depression and aggression. Accordingly, agents acting simultaneously as dopamine $D_2$ and/or $D_3$ antagonists, as SSRIs and as 5-$HT_{1A}$ antagonists may be particularly useful for the treatment of various psychiatric and neurological disorders, in particular certain psychotic disorders, most in particular schizophrenia with improved antipsychotic activity and with an improved antidepressant and/or anxiolytic effect.

BACKGROUND PRIOR ART

WO 99/55672 (American Home Products Corporation) discloses antipsychotic indole derivatives having $D_2$-receptor and 5-$HT_{1A}$ receptor affinity. The herein disclosed compounds differ structurally from the compounds according to the present invention in the substitution of the piperazinyl-moiety.

WO 03/002552 (Lundbeck A/S) and WO 03/002556 (Lundbeck A/S) disclose antipsychotic indole derivatives having dopamine $D_3$ and $D_4$-receptor and 5-$HT_{1A}$-receptor affinity. The herein disclosed compounds differ structurally from the compounds according to the present invention in the substitution pattern of the piperazinyl-moiety, as well as pharmacologically in their dopamine selectivity.

Compounds having only reported SSRI and 5-$HT_{1A}$ potency and having an indolyl- or indolyl-like moiety (such as an 1H-pyrrolo[2,3-b]pyridinyl-moiety) coupled to a cyclic amine moiety such as a piperazinyl-moiety or to a linear amine moiety, such as an ethylamine-moiety have been reported in WO 99/55672 (American Home Products Corporation), WO 00/40580 (American Home Products Corporation), WO 00/40581 (American Home Products Corporation), WO 00/64898 (American Home Products Corporation), EP 1 078 928 A1 (Adir et Compagnie), U.S. Pat. No. 6,313,126 (American Home Products Corporation), WO 02/085911 (Wyeth), WO 02/40465 (Wyeth), WO 02/48105 (Wyeth) and WO 03/010169 (Wyeth). None of these compounds have reported dopamine D2/D3 activity.

Compounds having reported SSRI activity and also showing an additional $\alpha_2$-adrenoceptor antagonist activity, while also comprising the isoxazoline moiety are known from WO02/066484, WO03/082878, WO04/016621, WO04/018482 and WO04/018483, all from Janssen Pharmaceutica NV, and from J. Ignacio Andres et al., *Bioorganic & Medicinal Chemistry Letters* 13 (2003) 2719-2725. None of these compounds have reported dopamine D2/D3 and 5$HT_{1A}$ activity. The herein disclosed compounds differ structurally from the compounds according to the present invention in the substitution pattern of the isoxazoline moiety.

DESCRIPTION OF THE INVENTION

It is the object of the present invention to provide the cited particular combination of therapeutic activities in one single molecule. It would have major advantages above polypharmacy by reducing drug-drug interactions, metabolic burden, and the adding-up of side effects, by simplifying treatment schedules (reduction of number of pills), and, thereby, enhance patient compliance. Additionally, it would have high potential in Bipolar Disorder and/or Personality Disorder, as $D_2$ antagonism would be beneficial in the maniac phase and 5HTT activity would be beneficial in the depression phase.

It is the further object of the present invention to provide compounds with a binding affinity towards dopamine receptors, in particular towards dopamine $D_2$ and/or $D_3$ receptors, which exhibit selective serotonin reuptake inhibition properties, and which should also show an affinity for the 5-$HT_{1A}$ receptor, in particular as an antagonist.

This goal was achieved by a novel isoxazoline-indol derivative according to the general Formula (I)

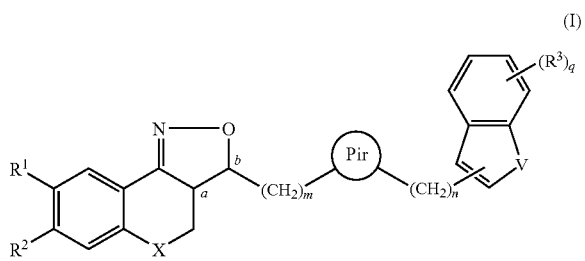

a pharmaceutically acceptable acid or base addition salt thereof, a stereochemically isomeric form thereof, an N-oxide form thereof or a quaternary ammonium salt thereof, wherein:

X is $CH_2$; $NR^4$; S or O; wherein $R^4$ is selected from the group of hydrogen, alkyl, Ar, Ar-alkyl, alkylcarbonyl, alkyloxycarbonyl and mono- and di(alkyl)aminocarbonyl;

V is S; O or $NR^5$; wherein $R^5$ is selected from the group of hydrogen and alkyl; or $R^5$ is a covalent bond between the nitrogen and the $(CH_2)_n$ moiety;

$R^1$ and $R^2$ are each, independently from each other, selected from the group of hydrogen; halo; hydroxy; amino; alkyl; Ar; heteroaryl; cyano; nitro; mono- and di(alkyl)amino; mono- and di(Ar)amino; mono- and di(heteroaryl)amino; mono- and di(alkylcarbonyl)amino; mono- and di(Ar-carbonyl)amino; mono- and di(heteroarylcarbonyl)amino; mono- and di(heteroarylalkyl)amino; alkyloxy; alkylcarbonyloxy; Ar-carbonyloxy; heteroarylcarbonyloxy; alkyloxyalkyloxy; alkyloxyalkyloxyalkyloxy; alkylcarbonyloxyalkyloxy; alkyloxyalkylcarbonyloxyalkyloxy and mono- and di(alkyl)aminocarbonyloxyalkyloxy; or $R^1$ and $R^2$ together may form a bivalent radical of formula —$OCH_2O$—; —$OCH_2CH_2O$— and —$OCH_2CH_2CH_2O$—;

$R^3$ is selected from the group of hydrogen; hydroxy; amino; nitro; cyano; halo; alkyl; alkyloxy; alkyloxyalkyloxy; alkyloxyalkyloxyalkyloxy; Ar; mono- and di(alkyl)aminocarbonylamino; mono- and di(Ar)aminocarbonylamino; mono- and di(alkyloxocarbonylcarbonyl)amino; mono- and di(alkylcarbonyl)amino; mono- and di(alkyloxoalkylcarbonyl)amino and mono- and di(alkylsulphonyl)amino;

q is an integer equal to zero; 1 or 2;

$(CH_2)_m$ is a covalent bond or a straight hydrocarbon chain of m carbon atoms, m being an integer equal to 1; 2 or 3;

$(CH_2)_n$ is a covalent bond or a straight hydrocarbon chain of n carbon atoms, n being an integer equal to 1; 2; 3 or 4;

Pir is a bivalent radical according to any one of Formula (IIa), (IIb) or (IIc), each radical optionally substituted with p radicals $R^6$, wherein:

(IIa)

(IIb)

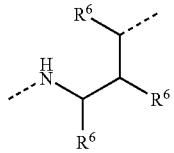

(IIc)

each $R^6$ is independently from each other, selected from the group of hydrogen; hydroxy; amino; nitro; cyano; halo and alkyl;

p is an integer equal to zero; 1 or 2;

Ar is phenyl or naphthyl; each radical optionally substituted with one or more halo, cyano, oxo, hydroxy, alkyl, formyl, alkyloxy or amino radicals;

heteroaryl represents a monocyclic heterocyclic radical selected from the group of azetidinyl; pyrrolidinyl; dioxolyl; imidazolidinyl; pyrrazolidinyl; piperidinyl; homopiperidinyl; dioxyl; morpholinyl; dithianyl; thiomorpholinyl; piperazinyl; imidazolidinyl; tetrahydrofuranyl; 2H-pyrrolyl; pyrrolinyl; imidazolinyl; pyrrazolinyl; pyrrolyl; imidazolyl; pyrazolyl; triazolyl; furanyl; thienyl; oxazolyl; isoxazolyl; thiazolyl; thiadiazolyl; isothiazolyl; pyridinyl; pyrimidinyl; pyrazinyl; pyridazinyl and triazinyl; each heterocyclic radical optionally substituted with one or more radicals selected from the group of alkyl, phenyl, phenyl substituted with alkyl, benzyl, halo, cyano, oxo, hydroxy, formyl, alkyloxy, alkylcarbonyl, tetrahydrofurylcarbonyl and amino; and alkyl represents a straight or branched saturated hydrocarbon radical having from 1 to 6 carbon atoms or a cyclic saturated hydrocarbon radical having from 3 to 6 carbon atoms, each hydrocarbon radical optionally substituted with one or more halo, cyano, oxo, hydroxy, formyl or amino radicals.

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable acid or base addition salt thereof, a stereochemically isomeric form thereof, an N-oxide form thereof or a quaternary ammonium salt thereof.

The invention also relates to the use of a compound according to the invention for the preparation of a medicament for the prevention and/or treatment of a disorder or disease responsive to the inhibition of dopamine $D_2$ and/or $D_3$ receptors.

The invention also relates to the use of a compound according to the invention for the preparation of a medicament for the prevention and/or treatment of a disorder or disease responsive to the inhibition of serotonin reuptake.

The invention also relates to the use of a compound according to the invention for the preparation of a medicament for the preparation of a medicament for the prevention and/or treatment of a disorder or disease responsive to the inhibition of 5-$HT_{1A}$ receptors.

The invention also relates to the use of a compound according to the invention for the preparation of a medicament for the preparation of a medicament for the prevention and/or treatment of a disorder or disease responsive to the combined effect of a dopamine $D_2$ antagonist, an SSRI and a 5-$HT_{1A}$ antagonist.

In particular, the invention relates to the use of a compound according to the invention for the preparation of a medicament for the prevention and/or treatment of affective disorders such as general anxiety disorder, panic disorder, obsessive compulsive disorder, depression, social phobia and eating disorders; and other psychiatric disorders such as, but not limited to psychosis and neurological disorders.

More in particular, the invention relates to the use of a compound according to the invention for the preparation of a medicament for the prevention and/or treatment of schizophrenia.

More in particular, the invention relates to the use of a compound according to the invention for the preparation of a medicament for the prevention and/or treatment of Bipolar Disorder and/or Personality Disorder.

DETAILED DESCRIPTION OF THE INVENTION

In a preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein X is O.

In a further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein one of $R^1$ and $R^2$ is methoxy, preferably both $R^1$ and $R^2$ are methoxy.

In a further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein the linker-moiety —$(CH_2)_m$— is —$CH_2$— and the linker moiety —$(CH_2)_n$— is a covalent bond or —$CH_2$—.

In a further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein Pir is a an unsubstituted bivalent radical according to any one of Formula (IIa) and (IIb), wherein $R^6$ is hydrogen and p=1, i.e. the preferred Pir radicals are unsubstituted.

In a further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein V is $NR^5$, wherein $R^5$ is defined as in Formula (I), $R^3$ is selected from the group of hydrogen, fluoro, chloro, bromo, cyano, methyl, amino, hydroxy, methoxy and nitro and q=1, i.e. the preferred embodiment is related to an indol-moiety substituted with said radicals $R^3$ and $R^5$.

In a further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein heteroaryl is selected from the group of pyrrolidinyl and morpholinyl.

In a further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein
X is O;
V is S; O or $NR^5$; wherein $R^5$ is selected from the group of hydrogen and alkyl; or $R^5$ is a covalent bond between the nitrogen and the $(CH_2)_n$ moiety;

$R^1$ and $R^2$ are each, independently from each other, selected from the group of hydrogen; mono- and di(alkylcarbonyl) amino; mono- and di(pyrrolidinylalkyl)amino; alkyloxy; alkyloxyalkyloxyalkyloxy; alkylcarbonyloxyalkyloxy; alkyloxyalkylcarbonyloxyalkyloxy; mono- and di(alkyl) aminocarbonyloxyalkyloxy and morpholinyl; or $R^1$ and $R^2$ together may form a bivalent radical of formula —$OCH_2CH_2O$—;
$R^3$ is selected from the group of hydrogen; hydroxy; amino; nitro; cyano; halo; alkyl; alkyloxy; alkyloxyalkyloxyalkyloxy; Ar; mono- and di(alkyl)aminocarbonylamino; mono- and di(Ar)aminocarbonylamino; mono- and di(alkyloxocarbonylcarbonyl)amino; mono- and di(alkylcarbonyl) amino; mono- and di(alkyloxoalkylcarbonyl)amino and mono- and di(alkylsulphonyl)amino;
q is an integer equal to zero or 1;
$(CH_2)_m$ a straight hydrocarbon chain of m carbon atoms, m being an integer equal to 1;
$(CH_2)_n$ is a covalent bond or a straight hydrocarbon chain of n carbon atoms, n being an integer equal to 1;
Pir is a bivalent radical according to any one of Formula (IIa), (IIb) or (IIc), each substituted with hydrogen radicals $R^6$;
Ar is phenyl; and
alkyl represents a straight or branched saturated hydrocarbon radical having from 1 to 2 carbon atoms; each radical optionally substituted with a hydroxy radical.

In the framework of this application, alkyl is defined as a monovalent straight or branched saturated hydrocarbon radical having from 1 to 6 carbon atoms, for example methyl, ethyl, propyl, butyl, 1-methylpropyl, 1,1-dimethylethyl, pentyl, hexyl; alkyl further defines a monovalent cyclic saturated hydrocarbon radical having from 3 to 6 carbon atoms, for example cyclopropyl, methylcyclopropyl, cyclobutyl, cyclopentyl and cyclohexyl. The definition of alkyl also comprises an alkyl radical that is optionally substituted on one or more carbon atoms with one or more phenyl, halo, cyano, oxo, hydroxy, formyl and amino radicals, for example hydroxyalkyl, in particular hydroxymethyl and hydroxyethyl and polyhaloalkyl, in particular difluoromethyl and trifluoromethyl.

In the framework of this application, halo is generic to fluoro, chloro, bromo and iodo.

In the framework of this application, with "compounds according to the invention" is meant a compound according to the general Formula (I), a pharmaceutically acceptable acid or base addition salt thereof, a stereochemically isomeric form thereof, an N-oxide form thereof or a quaternary ammonium salt thereof.

The pharmaceutically acceptable acid addition salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely said acid addition salt forms can be converted into the free base form by treatment with an appropriate base.

The compounds according to Formula (I) containing acidic protons may also be converted into their therapeutically active non-toxic metal or amine addition salts forms (base addition salts) by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate acid.

Quaternary ammonium salts of compounds according to Formula (I) defines said compounds which are able to form by a reaction between a basic nitrogen of a compound according to Formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has a positively charged nitrogen. Pharmaceutically acceptable counterions include chloro, bromo, iodo, trifluoroacetate and acetate ions.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g. of the piperazinyl or piperidinyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

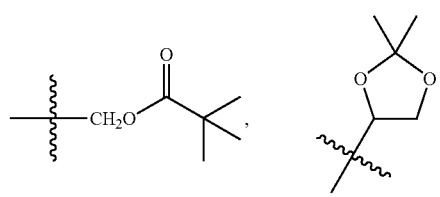

Amidated groups include groups of the formula —CONR$^y$R$^z$, wherein R$^y$ is H, C$_{1-6}$alkyl, phenyl or benzyl and R$^z$ is —OH, H, $C_{1-6}$alkyl, phenyl or benzyl. Compounds according to the invention having an amino group may be derivatised with a ketone or an aldehyde such as formaldehyde to form a Mannich base. This base will hydrolyze with first order kinetics in aqueous solution.

Preparation

The compounds according to the invention can generally be prepared by a succession of steps, each of which is known to the skilled person.

The compounds of the present invention can generally be prepared by alkylating a mesylate intermediate of Formula (III) with an intermediate of Formula (IV). The reaction can be performed in a reaction-inert solvent such as, for example, methylisobutylketone (MIK), in the presence of a catalyst, such as, for example potassium iodide, and optionally in the presence of a suitable base such as, for example, sodium carbonate or potassium carbonate. Stirring may enhance the rate of the reaction. The reaction may conveniently be carried out at a temperature ranging between room temperature and the reflux temperature of the reaction mixture and, if desired, the reaction may be carried out in an autoclave at an increased pressure.

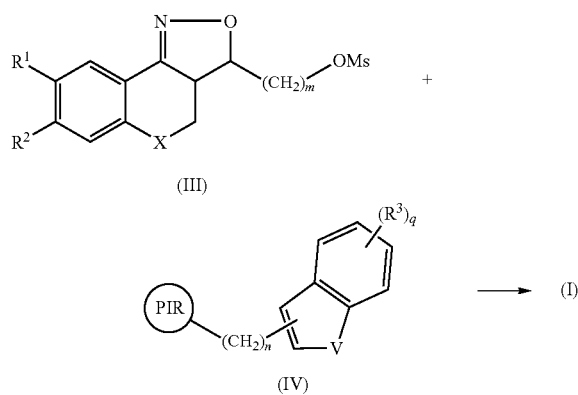

Compounds of Formula (I) can also be prepared by reductively aminating an aldehyde intermediate of Formula (V) following art-known reductive amination procedures with an intermediate of Formula (IV).

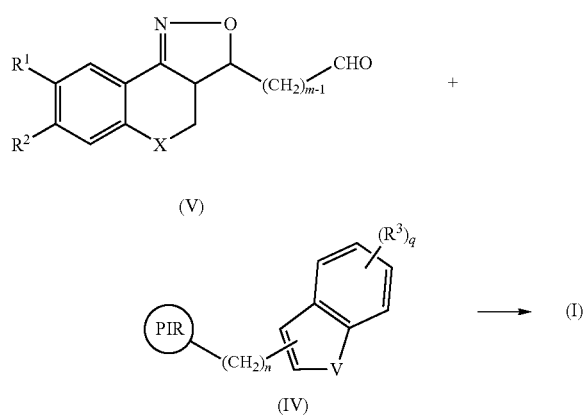

Said reductive amination can be performed in a reaction-inert solvent such as, for example, a mixture of THF and acetic acid, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal, rhodium-on-carbon or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

The compounds of Formula (I) may further be prepared by converting compounds of Formula (I) into each other according to art-known group transformation reactions, and further, if desired, by converting the compounds of Formula (I), into a therapeutically active non-toxic acid addition salt by treatment with an acid, or into a therapeutically active non-toxic base addition salt by treatment with a base, or conversely, by converting the acid addition salt form into the free base by treatment with alkali, or converting the base addition salt into the free acid by treatment with acid; and, if desired, by preparing stereochemically isomeric forms, N-oxides thereof and quaternary ammonium salts thereof. Examples of such conversion have been given in the Experimental section.

The starting materials and some of the intermediates are known compounds and are commercially available or may be prepared according to conventional reaction procedures generally known in the art. In particular, the preparation of the isoxazoline-moieties is described a.o. in WO02/066484, WO03/082878, WO04/016621, WO04/018482 and WO04/018483, all from Janssen Pharmaceutica NV. In particular, tetrahydropyridyl- and piperidinyl-indole-derivatives were prepared as previously described in EP 705600.

Compounds of Formula (I) and some of the intermediates may have at least two stereogenic centers in their structure (carbon atoms denoted a and b in Formula (I)), present in a R or a S configuration.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

The compounds according to the invention, in particular compounds according to Formula (I), the pharmaceutically acceptable acid or base addition salts thereof, a stereochemically isomeric form thereof, an N-oxide form thereof or a quaternary ammonium salt thereof, have surprisingly been shown to have a binding affinity towards dopamine receptors, in particular towards dopamine $D_2$ and/or $D_3$ receptors, with selective serotonin reuptake inhibition (SSRI) properties and showing an affinity for the $5\text{-HT}_{1A}$ receptor, in particular as an antagonist and show a strong antidepressant and/or anxiolytic activity and/or antipsychotic activity.

In vitro receptor and neurotransmitter transporter binding and signal-transduction studies can be used to evaluate the dopamine antagonism activity and serotonin (5-HT) reuptake inhibitor activity of the present compounds. As indices for central penetration and potency to block the dopamine and serotonin transporters, respectively, ex vivo dopamine and serotonin transporter occupancy can be used. As indices of serotonin (5-HT) reuptake inhibition activity, the inhibition of head-twitches and excitation in rats, observed after subcutaneous injection or oral dosage of the compound before subcutaneous p-chloroamphetamine administration in rats can be used (pCA-test).

In view of their above mentioned potency, the compounds according to the invention are suitable for the prevention and/or treatment in diseases where either one of the activities alone or the combination of said activities may be of therapeutic use. In particular, the compounds according to the invention may be suitable for treatment and/or prophylaxis in the following diseases:

Central nervous system disorders, including:

Mood disorders, including particularly major depressive disorder, depression with or without psychotic features, catatonic features, melancholic features, atypical features of postpartum onset and, in the case of recurrent episodes, with or without seasonal pattern, dysthymic disorder, bipolar I disorder, bipolar II disorder, cyclothymic disorder, recurrent brief depressive disorder, mixed affective disorder, bipolar disorder not otherwise specified, mood disorder due to a general medical condition, substance-induced mood disorder, mood disorder not otherwise specified, seasonal affective disorder and premenstrual dysphoric disorders.

Anxiety disorders, including panic attack, agoraphobia, panic disorder without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder and anxiety disorder not otherwise specified.

Stress-related disorders associated with depression and/or anxiety, including acute stress reaction, adjustment disorders (brief depressive reaction, prolonged depressive reaction, mixed anxiety and depressive reaction, adjustment disorder with predominant disturbance of other emotions, adjustment disorder with predominant disturbance of conduct, adjustment disorder with mixed disturbance of emotions and conduct, adjustment disorders with other specified predominant symptoms) and other reactions to severe stress.

Dementia, amnesic disorders and cognitive disorders not otherwise specified, especially dementia caused by degenerative disorders, lesions, trauma, infections, vascular disorders, toxins, anoxia, vitamin deficiency or endocrinic disorders, or amnesic disorders caused by alcohol or other causes of thiamine deficiency, bilateral temporal lobe damage due to Herpes simplex encephalitis and other limbic encephalitis, neuronal loss secondary to anoxia/hypoglycaemia/severe convulsions and surgery, degenerative disorders, vascular disorders or pathology around ventricle III.

Cognitive disorders due to cognitive impairment resulting from other medical conditions.

Personality disorders, including paranoid personality disorder, schizoid personality disorder, schizotypical personality disorder, antisocial personality disorder, borderline personality disorder, histrionic personality disorder, narcissistic personality disorder, avoidant personality disorder, dependent personality disorder, obsessive-compulsive personality disorder and personality disorder not otherwise specified.

Schizoaffective disorders resulting from various causes, including schizoaffective disorders of the manic type, of the depressive type, of mixed type, paranoid, disorganized, catatonic, undifferentiated and residual schizophrenia, schizophreniform disorder, schizoaffective disorder, delusional disorder, brief psychotic disorder, shared psychotic disorder, substance-induced psychotic disorder and psychotic disorder not otherwise specified.

Akinesia, akinetic-rigid syndromes, dyskinesia and medication-induced parkinsonism, Gilles de la Tourette syndrome and its symptoms, tremor, chorea, myoclonus, tics and dystonia.

Attention-deficit/hyperactivity disorder (ADHD).

Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification.

Dementia of the Alzheimer's type, with early or late onset, with depressed mood.

Behavioural disturbances and conduct disorders in dementia and the mentally retarded, including restlessness and agitation.

Extra-pyramidal movement disorders.

Down's syndrome.

Akathisia.

Eating Disorders, including anorexia nervosa, atypical anorexia nervosa, bulimia nervosa, atypical bulimia nervosa, overeating associated with other psychological disturbances, vomiting associated with other psychological disturbances and non-specified eating disorders.

AIDS-associated dementia.

Chronic pain conditions, including neuropathic pain, inflammatory pain, cancer pain and post-operative pain following surgery, including dental surgery. These indications might also include acute pain, skeletal muscle pain, low back pain, upper extremity pain, fibromyalgia and myofascial pain syndromes, orofascial pain, abdominal pain, phantom pain, tic douloureux and atypical face pain, nerve root damage and arachnoiditis, geriatric pain, central pain and inflammatory pain.

Neurodegenerative diseases, including Alzheimer's disease, Huntington's chorea, Creutzfeld-Jacob disease, Pick's disease, demyelinating disorders, such as multiple sclerosis and ALS, other neuropathies and neuralgia, multiple sclerosis, amyotropical lateral sclerosis, stroke and head trauma.

Addiction disorders, including:

Substance dependence or abuse with or without physiological dependence, particularly where the substance is alcohol, amphetamines, amphetamine-like substances, caffeine, cannabis, cocaine, hallucinogens, inhalants, nicotine, opioids, phencyclidine, phencyclidine-like compounds, sedative-hypnotics, benzodiazepines and/ or other substances, particularly useful for treating withdrawal from the above substances and alcohol withdrawal delirium.

Mood disorders induced particularly by alcohol, amphetamines, caffeine, cannabis, cocaine, hallucinogens, inhalants, nicotine, opioids, phencyclidine, sedatives, hypnotics, anxiolitics and other substances.

Anxiety disorders induced particularly by alcohol, amphetamines, caffeine, cannabis, cocaine, hallucinogens, inhalants, nicotine, opioids, phencyclidine, sedatives, hypnotics, anxiolitics and other substances and adjustment disorders with anxiety.

Smoking cessation.

Body weight control, including obesity.

Sleep disorders and disturbances, including:

Dyssomnias and/or parasomnias as primary sleep disorders, sleep disorders related to another mental disorder, sleep disorder due to a general medical condition and substance-induced sleep disorder.

Circadian rhythms disorders.

Improving the quality of sleep.

Sexual dysfunction, including sexual desire disorders, sexual arousal disorders, orgasmic disorders, sexual pain disorders, sexual dysfunction due to a general medical condition, substance-induced sexual dysfunction and sexual dysfunction not otherwise specified.

The invention therefore relates to a compound according to the general Formula (I), a pharmaceutically acceptable acid or base addition salt thereof, a stereochemically isomeric form thereof, an N-oxide form thereof or a quaternary ammonium salt thereof, for use as a medicine.

The invention also relates to the use of a compound according to the invention for the preparation of a medicament for the prevention and/or treatment of a disorder or disease responsive to the inhibition of dopamine $D_2$ and or $D_3$ receptors.

The invention also relates to the use of a compound according to the invention for the preparation of a medicament for the prevention and/or treatment of a disorder or disease responsive to the inhibition of 5-$HT_{1A}$ receptors.

The invention also relates to the use use of a compound according to the invention for the preparation of a medicament for the preparation of a medicament for the prevention and/or treatment of a disorder or disease responsive to the combined effect of a dopamine $D_2$ antagonist, an SSRI and a 5-$HT_{1A}$ antagonist.

The present invention also relates to a method for the prevention and/or treatment of dopamine-mediated diseases, in particular for the prevention and/or treatment of affective disorders such as general anxiety disorder, panic disorder, obsessive compulsive disorder, depression, social phobia and eating disorders; and other psychiatric disorders such as, but not limited to psychosis and neurological disorders, comprising administering to a human in need of such administration an effective amount of a compound according to the invention, in particular according to Formula (I), a pharmaceutically acceptable acid or base addition salt thereof, a stereochemically isomeric form thereof, an N-oxide form thereof or a quaternary ammonium salt thereof.

More in particular, the present invention relates to the use of a compound according to the invention for the preparation of a medicament for the prevention and/or treatment of schizophrenia.

More in particular, the present invention relates to the use of a compound according to the invention for the preparation of a medicament for the prevention and/or treatment of Bipolar Disorder and/or Personality Disorder.

Pharmaceutical Compositions

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable acid or base addition salt thereof, a stereochemically isomeric form thereof, an N-oxide form thereof or a quaternary ammonium salt thereof.

The compounds according to the invention, in particular the compounds according to Formula (I), the pharmaceutically acceptable acid or base addition salt thereof, a stereochemically isomeric form thereof, an N-oxide form thereof or a quaternary ammonium salt thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable dopamine antagonists, pharmaceutical compositions comprising said compounds for administration orally are especially advantageous.

The following examples are intended to illustrate but not to limit the scope of the present invention.

Experimental Part

A. Preparation of the Intermediate Compounds

Hereinafter "RT" means room temperature, "CDI" means 1,1'-carbonyldiimidazole, "DIPE" means diisopropylether, "MIK" means methylisobutylketone, "BINAP" means [1,1'-binaphthalene]-2,2'-diylbis[diphenylphosphine], "NMP" means 1-methyl-2-pyrrolidinone, "Pd$_2$(dba)$_3$" means tris(dibenzylideneacetone)dipalladium and "DMF" means N,N-dimethylformamide.

EXAMPLE A1

Preparation of Intermediate Compound 1 and 2

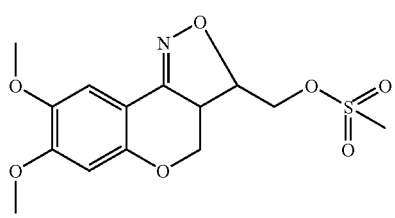

Intermediate compound 1
A-cis

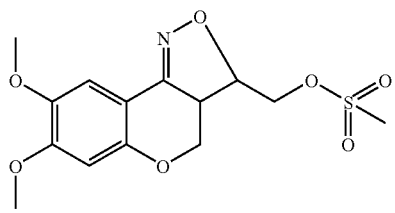

Intermediate compound 2
3S-cis 3a,4-Dihydro-7,8-dimethoxy-3H-[1]benzopyrano[4,3-c]isoxazole-3-methanol methanesulfonate ester (prepared according to teachings in WO2004/018482 of which the content is herein included) (200 g, 0.58 mol) was separated into its enantiomers by chiral column chromatography over column LC110-2 with stationary phase CHIRALPAK-AD (2000 g, packing pressure: 45 bar, detector range: 2.56, wavelength: 240 nm, temperature: 30° C.; injection solution: 200 g in 8.4 l CH$_3$CN; then, 19.6 l methanol (+2% ethanol) was added, then filtered; injection-volume: 700 ml; eluent: CH$_3$OH/CH$_3$CN 70/30 v/v). Two product fraction groups were collected and their solvent was evaporated. Yield: 105 g of intermediate compound 1 and 95 g of intermediate compound 2.

EXAMPLE A2 a. Preparation of Intermediate Compound 3

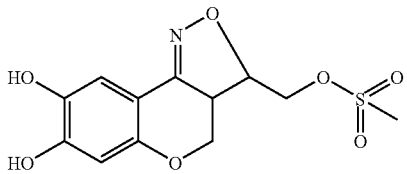

BBr$_3$ (99.9%) (0.5096 mol) was added dropwise to a mixture of intermediate compound 2 (prepared according to A1) (0.1019 mol) in CH$_2$Cl$_2$ (1225 ml) under N$_2$ atmosphere and at −78° C. The reaction mixture was stirred at −40° C. for 3 hours, then extra BBr$_3$ (99.9%) (0.063 mol) was added and the mixture was stirred at −40° C. for 30 minutes. The reaction mixture was poured out into ice-water and filtered over Celite. The solid residue was washed with CH$_2$Cl$_2$/CH$_3$OH, giving precipitate (I). The filtrate was extracted with CH$_2$Cl$_2$, dried over Na$_2$SO$_4$, filtered and the solvent was evaporated dry. The residue was purified by several HPLC's (eluent 1: CH$_2$Cl$_2$/(CH$_3$OH/NH$_3$) 99/1; eluent 2: EtOAc/(CH$_3$OH/NH$_3$) 99/1, 98/2). Two product fractions were collected and each solvent was evaporated (Yield Fraction 1: 9.12 g (27%) and Fraction 2: 6.18 g (18%)). Precipitate (I) was dissolved in CH$_2$Cl$_2$/CH$_3$OH (20%) and filtered. The filtrate was evaporated dry and the residue was washed with CH$_2$Cl$_2$/CH$_3$OH (4%), filtered off and dried. Yield: 0.89 g of intermediate compound 3 (B-(3α, 3α)) (2.6%).

b. Preparation of Intermediate Compound 4

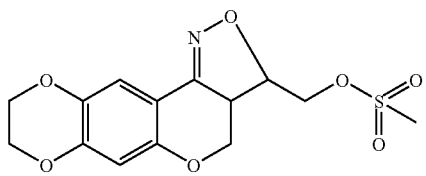

K$_2$CO$_3$ (0.00336 mol) and 1,2-dibromoethane (0.0018 mol, 99%) were added to a mixture of intermediate compound 3 (0.00168 mol) in N,N-dimethylformamide (5 ml) in a sealed tube, then the reaction mixture was stirred overnight at room temperature, washed with water and extracted with EtOAc. The organic layer was dried over Na$_2$SO$_4$, filtered and the solvent was evaporated dry. The residue was purified by open column chromatography (eluent 1: CH$_2$Cl$_2$; eluent 2: CH$_2$Cl$_2$/CH$_3$OH 99/1). The product fractions were collected and the solvent was evaporated. Yield: 0.24 g of intermediate compound 4 (B-(3α, 3aα)) (41%).

EXAMPLE A3

Preparation of Intermediate Compound 5

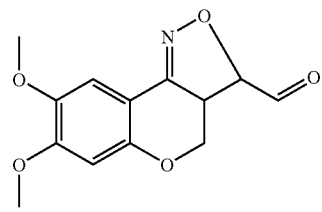

Dess-Martin periodinane (0.0021 mol) was added to a solution of 3a,4-dihydro-7,8-dimethoxy-3H-[1]benzopyrano[4,3-c]isoxazole-3-methanol (prepared according to teachings in WO2004/018482 of which the content is herein included) (0.0019 mol) in $CH_2Cl_2$ (50 ml). The reaction mixture was stirred for 20 minutes at room temperature. A saturated $NaHCO_3$ solution and $Na_2SO_4$ was added. The mixture was stirred for 10 minutes. The separated organic layer was washed with brine and $H_2O$, dried ($Na_2SO_4$), filtered and the solvent was evaporated. The residue was taken up in cold $Et_2O$. The precipitate was filtered off, washed and dried. Yield: 320 mg of intermediate compound 5 ((3α, 3aα) racemic mixture).

EXAMPLE A4 a. Preparation of Intermediate Compound 6

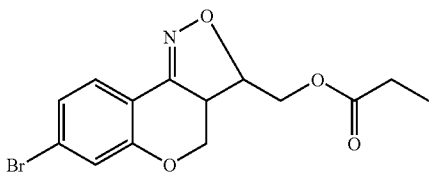

A mixture of 5-bromo-salicylaldehyde (3 g, 14.9 mmol), $K_2CO_3$ (4.12 g, 29.8 mmol) and (E)-ethyl 4-bromocrotonate (3 ml, 22.3 mmol) in anhydrous dimethylformamide (17 ml) was stirred at room temperature for 4 h. When the TLC analysis showed the disappearance of starting material, the crude reaction mixture was filtered through a CELITE pad and the filtrate was concentrated in vacuo. The residue was diluted with water (17 ml) and extracted with dichloromethane (3×17 ml). The organic phase was dried and concentrated in vacuo. The residue was precipitated with DIPE, affording 3.11 g (61% yield) of 4-(2-formyl-5-bromophenoxy)but-2(E)-enoic acid ethyl ester. To a solution of previous prepared ester (3.11 g, 9.9 mmol) in absolute ethanol (25 mL), hydroxylamino hydrochloride (0.83 g, 11.9 mmol) and sodium acetate (1.22 g, 14.8 mmol) were added. After 2 hours at room temperature, the TLC analysis showed the absence of starting material. The solvent was evaporated in vacuo and the residue was dissolved in water (20 ml) and extracted with dichloromethane (3×30 ml). The organic layer was dried ($Na_2SO_4$) and concentrated at reduced pressure to yield 3.95 g (quantitative yield) of 4-[2-(hydroxyiminomethyl)-5-bromophenoxy]but-2(E)-enoic acid ethyl ester used in the next reaction step without further purification. To a solution of previous synthesized oxime (3.8 g, 11.6 mmol) in dichloromethane (47 ml), 4% aqueous solution of sodium hypochlorite (40 ml, 23.1 mmol) was added portionwise and the reaction was stirred for 2 hours at room temperature. After that, triethylamine (2.4 ml, 17.4 mmol) was added dropwise at 0° C. The reaction was stirred overnight at room temperature. Then, the organic layer was separated, dried with anhydrous $Na_2SO_4$, filtered and the solvent evaporated. The residue was purified by column chromatography (dichloromethane). Yield: 1.71 g of intermediate compound 6 ((7-bromo-3a,4-dihydro-3H-[1]benzopyrano[4,3-c]isoxazole-3-carboxylic acid ethyl ester) 45% ((3α, 3aα) racemic mixture).

b. Preparation of Intermediate Compound 7

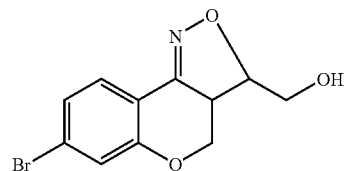

To a solution of intermediate compound 6 (3.3 g, 0.0101 mol) in 84 ml of mixture $THF/H_2O$ (10/1) at 0° C., $NaBH_4$ (0.96 g, 0.0253 mol) was portionwise added and then the mixture was stirred at room temperature for 24 hours. Then $NH_4Cl$ saturated aqueous solution was added and the organic layer was separated, dried over $Na_2SO_4$ filtered and evaporated yielding 3.01 g of intermediate compound 7 ((3α, 3aα) racemic mixture).

c. Preparation of Intermediate Compound 8

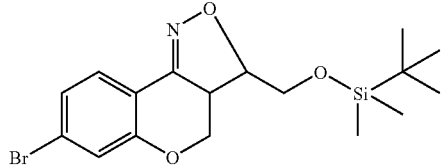

A mixture of intermediate compound 7 (0.031 mol), chloro (1,1-dimethylethyl)dimethylsilane (0.031 mol) and 1H-imidazole (0.031 mol) in $CH_2Cl_2$ (100 ml) was stirred for 16 hours at room temperature and $H_2O$ was added. The organic layer was separated, dried ($Na_2SO_4$), filtered off and the solvent was evaporated. The residue was purified by short open column chromatography over silica gel (eluent gradient: Heptane/EtOAc 80/20, 66/33, 50/50). The product fractions were collected and the solvent was evaporated. Yield: 10 g of intermediate compound 8 (83%) ((3α,3aα) racemic mixture).

d. Preparation of Intermediate Compound 9

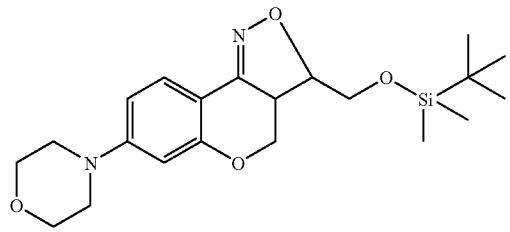

A mixture of intermediate compound 8 (0.0038 mol), morpholine (0.0092 mol), acetic acid, palladium (2+) salt (0.052 g, 47.5%), BINAP (0.00034 mol) and $Cs_2CO_3$ (0.01064 mol) in toluene (dry and degassed) (25 ml) was stirred for 16 hours in a sealed tube at 100° C. under $N_2$, then the reaction mixture was filtered over celite and the path was washed with EtOAc. The filtrate was evaporated and the residue was purified by short open column chromatography over silica gel (eluent gradient gradient: Heptane/EtOAc 66/33, 50/50). The product fractions were collected and the solvent was evaporated. Yield: 0.769 g of intermediate compound 9 (50%) ((3α,3aα) racemic mixture).

e. Preparation of Intermediate Compound 10

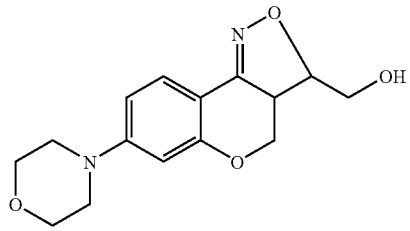

A mixture of intermediate compound 9 (0.0019 mol) and N,N,N-tributylbutanaminium fluoride (0.00288 mol; 1M in THF) in dry THF (10 ml) was reacted for 16 hours at room temperature under $N_2$ and then the reaction mixture was taken up in $H_2O$/EtOAc. The organic layer was separated, dried ($Na_2SO_4$), filtered off and the solvent was evaporated. Yield: 0.550 g of intermediate compound 10 (100%) ((3α,3aα) racemic mixture).

f. Preparation of Intermediate Compound 11

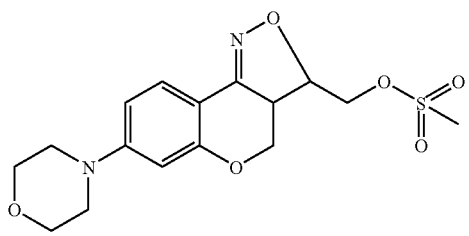

A mixture of intermediate compound 10 (0.0019 mol), methanesulfonyl chloride (0.00285 mol) and $Et_3N$ (0.0038 mol) in $CH_2Cl_2$ (20 ml) was stirred for 2 hours at room temperature and then $H_2O$ was added. The organic layer was separated, dried ($Na_2SO_4$), filtered off and the solvent was evaporated. The residue was purified by short open column chromatography over silica gel (eluent: EtOAc 100%). The product fractions were collected and the solvent was evaporated. Yield: 0.300 g of intermediate compound 11 (43%) ((3α,3aα) racemic mixture).

EXAMPLE A5 a. Preparation of Intermediate Compound 12 and 13

Intermediate 12

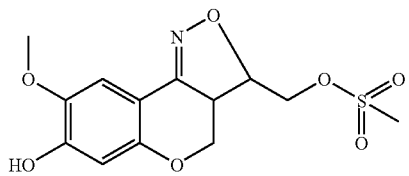

-continued

Intermediate 13

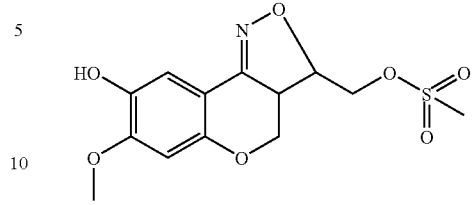

Reaction was done under $N_2$ flow. To a solution of intermediate compound 2 (prepared according to A1) (0.017 mol) in $CH_2Cl_2$ (200 ml) shuttled at −78° C., $BBr_3$ (0.087 mol) was added dropwise. The reaction mixture was allowed to warm to −40° C. and was stirred for 2 hours. The mixture was poured out into ice-water and extracted with a solution of $CH_2Cl_2$/$CH_3OH$ 95/5 and AcOEt. The combined separated organic layers were dried ($MgSO_4$) and the solvent was evaporated. The residue was separated and purified by high-performance liquid chromatography over silica gel (eluent: $CH_2C_2$/(MeOH/$NH_3$) 98/2). The product fractions were collected and the solvent was evaporated. Yield: 2.43 g intermediate compound 12 (43%; B-(3α, 3aα)) and 1.75 g of intermediate compound 13 (31%; B-(3α, 3aα)).

b. Preparation of Intermediate Compound 14

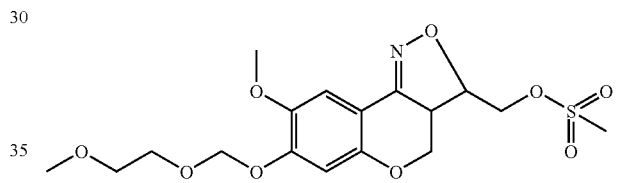

$Cs_2CO_3$ (0.0022774 mol) was added to a solution of intermediate compound 12 (0.0015183 mol) in 2-propanone (15 ml) and the mixture was cooled on an ice water bath, then a solution of 1-(chloromethoxy)-2-methoxyethane (0.0022774 mol) in 2-propanone (q.s.) was added dropwise and the reaction mixture was stirred overnight in a Parr reactor vessel at 50° C. The mixture was cooled and the solvent was evaporated. The residue was partitioned between $CH_2Cl_2$/$H_2O$ and the organic layer was separated. The aqueous layer was extracted 2 times with $CH_2Cl_2$. The organic layers were combined, dried ($Na_2SO_4$), filtered off and the solvent was evaporated. The residue was crystallised from $CH_3CN$/DIPE and the resulting precipitate was collected. Yield: 0.560 g of intermediate compound 14 (88%; (B-(3α,3aα)).

c. Preparation of Intermediate Compound 18

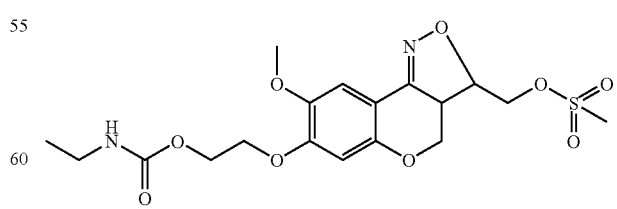

To a mixture of intermediate compound 12 (prepared according to A5.a) (1.0 g, 3 mmol) and $K_2CO_3$ (1.26 g, 9.1 mmol) in a Parr pressure reactor vessel was added a solution of 2-bromoethyl ethylcarbamic acid ester (1.61 g, 7 mmol) in DMF (30 ml). The resulting mixture was stirred at room temperature for 16 hours and then more 2-bromoethyl ethylcarbamic acid ester (0.8 g, 3.5 mmol) and K$_2$CO$_3$ (0.63 g, 4.5 mmol) were added and the mixture was stirred for 3 days. The crude reaction was washed with H$_2$O and then extracted with AcOEt. The organic layer was separated, dried over Na$_2$SO$_4$, filtered an evaporated. The residue was purified by short open column chromatography over silica gel (eluent gradient CH$_2$Cl$_2$/acetone 90/10 and 85/15). Desired fractions were collected and evaporated. Yield: 1.19 g of intermediate compound 18 (89%, B-(3α, 3aα)).

EXAMPLE A6 a. Preparation of Intermediate Compound 15

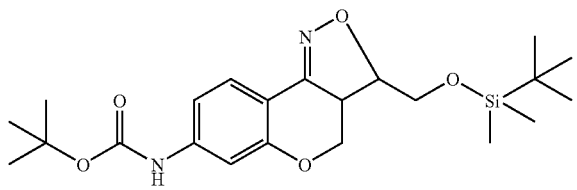

A mixture of intermediate compound 8 (prepared according to A4.c) (1.6 g, 4.06 mmol), tert-butyl carbamate (0.56 g, 4.82 mmol), Pd(OAc)$_2$ (72 mg, 0.32 mmol), Xantphos (256 mg, 0.442 mmol) and Cs$_2$CO$_3$ (3.4 g, 10.44 mmol) in 20 ml of dioxane (dry and degassed) was stirred at 110° C. in a sealed tube for 16 hours. After cooling to room temperature the mixture was filtered off through a celite pad and the filtrate was evaporated. The residue was purified by short open column chromatography over silica gel (eluent CH$_2$C$_2$/(MeOH/NH$_3$ saturated solution) 95/5). Desired fractions were collected and evaporated. Yield: 1.70 g of intermediate compound 15 (100%, (3α, 3aα) racemic mixture).

b. Preparation of Intermediate Compound 16

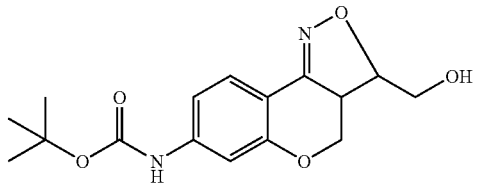

To a solution of intermediate compound 15 (1.73 g, 4.02 mmol) in 50 ml of THF was added tetrabutylammonium fluoride (1.8 ml, 6.02 mmol). The mixture was stirred at room temperature for 16 hours and then NH$_4$Cl saturated aqueous solution was added and the mixture was stirred for 10 minutes more. Then the organic layer was separated and the aqueous layer extracted with CH$_2$Cl$_2$. The combined organic extracts were dried (Na$_2$SO$_4$) filtered and evaporated. The residue was purified by short open column chromatography over silica gel (eluent CH$_2$C$_2$/(MeOH/NH$_3$ saturated solution) 95/5). Desired fractions were collected and evaporated. Yield: 1.16 g of intermediate compound 16 (90%; ((3α, 3aα) racemic mixture).

c. Preparation of Intermediate Compound 17

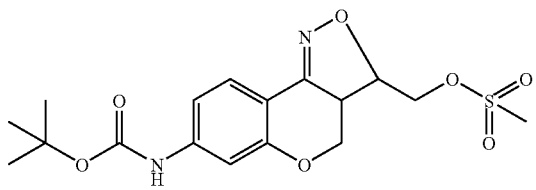

A solution of intermediate compound 16 (1.16 g, 3.62 mmol) in CH$_2$Cl$_2$ (50 ml) was cooled to 0° C. and then triethylamine (1 ml, 7.24 mmol) was dropwise added. The mixture was stirred for 30 minutes and then mesyl chloride was dropwise added. The mixture was stirred at 0° C. for 1 hour and then H$_2$O was added. The organic layer was separated, dried over Na$_2$SO$_4$, filtered and evaporated. The residue was precipitated from CH$_3$CN. The solid was filtered off and dried. Yield: 626 mg of intermediate compound 17 (45%; (3α, 3aα) racemic mixture).

EXAMPLE A7

Preparation of Intermediate Compound 19

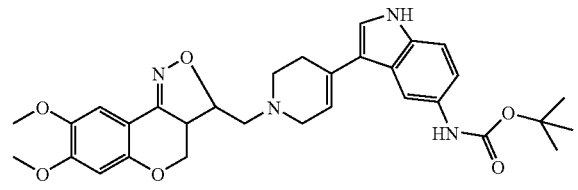

A mixture of 3a,4-dihydro-7,8-dimethoxy-3H-[1]benzopyrano[4,3-c]isoxazole-3-methanol methanesulfonate ester (Prepared according to teachings in WO2004/018482, of which the content is herein included) (0.0146 mol), 5-(tert-butoxycarbonyl)amino-3-(1,2,3,6-tetrahydro-4-pyridinyl)-1H-indole (0.016 mol), KI (catalytic quantity) and K$_2$CO$_3$ (0.016 mol) in MIK (q.s.) was stirred and refluxed overnight, then cooled and the crude reaction mixture was washed with water, then extracted with EtOAc. The separated organic layer was dried (Na$_2$SO$_4$), filtered and the solvent evaporated. The residue was purified by flash column chromatography over silica gel (eluent gradient: CH$_2$Cl$_2$/CH$_3$OH 99/1 and 98/2). The product fractions were collected and the solvent was evaporated. Yield: 5.8 g of intermediate compound 19 (69%; (3α, 3aα) racemic mixture)).

EXAMPLE A8

Preparation of Intermediate Compound 20

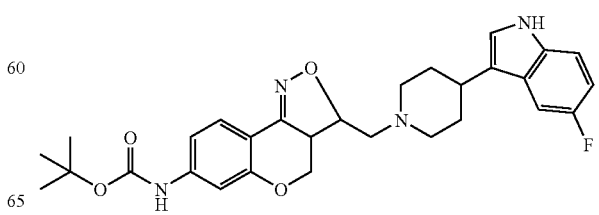

A mixture of methanesulfonic acid 7-tert-butoxycarbonylamino-3a,4-dihydro-3H-chromeno[4,3-c]isoxazol-3-ylmethyl ester (0.31 g, 0.81 mmol), B (0.21 g, 0.98 mmol), $K_2CO_3$ (0.22 g, 1.63 mmol) and KI (0.13 g, 0.81 mmol) in methyl isobutyl ketone (10 ml) was stirred at 120° C. for 16 hours. Then the solvent was evaporated until dryness and the residue partitioned between $CH_2Cl_2$ and $H_2O$. The organic layer was separated, dried over $Na_2SO_4$, filtered and evaporated. The residue was purified by short open column chromatography over silica gel (eluent $CH_2C_2$/(MeOH/$NH_3$ sat) 98/2 and 95/5). Desired fractions were collected and evaporated yielding 0.30 g of compound 20. Y: 71%.

B. Preparation of the Final Compounds

EXAMPLE B1

Preparation of Final Compound 1

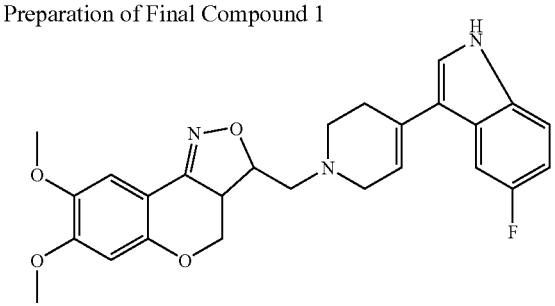

A mixture of 3a,4-dihydro-7,8-dimethoxy-3H-[1]benzopyrano[4,3-c]isoxazole-3-methanol methanesulfonate ester (Prepared according to teachings in WO2004/018482, of which the content is herein included) (0.0014 mol), 5-fluoro-3-(1,2,3,6-tetrahydro-4-pyridinyl)-1H-indole (0.0021 mol), KI (0.0014 mol) and $K_2CO_3$ (0.0014 mol) in MIK (20 ml) was stirred and refluxed overnight, then cooled and the crude reaction mixture was washed with water, then extracted with EtOAc. The separated organic layer was dried ($Na_2SO_4$), filtered and the solvent evaporated. The residue was purified by flash column chromatography over silica gel (eluent gradient: $CH_2Cl_2$/$CH_3OH$ 99/1 and 98/2). The product fractions were collected and the solvent was evaporated. Yield: 0.18 g of final compound 1 (26%; (3α, 3aα) racemic mixture)).

Note: Final compound 28 and 29 were prepared according to B1 with the use of intermediate 3 (prepared according to A2.b) instead of 3a,4-dihydro-7,8-dimethoxy-3H-[1]benzopyrano[4,3-c]isoxazole-3-methanol methanesulfonate ester as described above.

EXAMPLE B2

Preparation of Final Compound 54

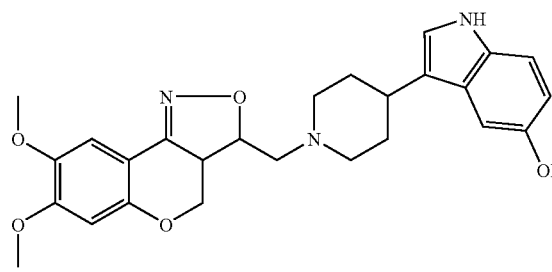

A mixture of intermediate compound 5 (prepared according to A3) (0.00095 mol), 3-(4-piperidinyl)-1H-indol (0.00085 mol) and sodium cyanoborohydride (0.00142 mol) in THF/AcOH (8/2) (10 ml) was stirred for 16 hours at room temperature, then the reaction mixture was diluted with $CH_2Cl_2$ and extracted with a 10% aqueous citric acid solution. The aqueous layer was alkalised with a saturated. $Na_2CO_3$ solution and extracted with $CH_2Cl_2$. The organic layer was separated, dried ($Na_2SO_4$), filtered off and the solvent was evaporated. The residue was purified by CC-LC on Chromatotron (eluent gradient: $CH_2Cl_2$/($CH_3OH$/$NH_3$) 98/2, 97/3, 96/4). The product fractions were collected and the solvent was evaporated. The residue was crystallised from $CH_2Cl_2$/DIPE, then the resulting precipitate was filtered off and dried. Yield: 0.035 g of final compound 54 (8%; (3α, 3aα) racemic mixture)).

EXAMPLE B3

Preparation of Final Compound 21

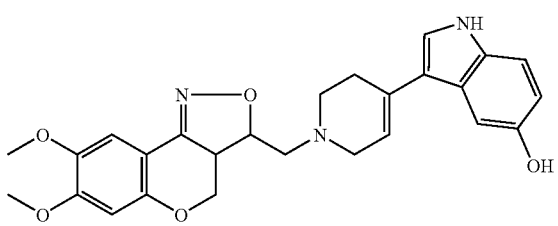

Sodium triacetoxy borohydride (0.010 mol) was slowly added to a solution of intermediate compound 5 (prepared according to A3) (0.0091 mol), 3-(1,2,3,6-tetrahydro-4-pyridinyl)-1H-indole-5-ol (0.010 mol) and acetic acid (catalytic quantity) in $CH_2Cl_2$ (100 ml) and the reaction mixture was stirred at room temperature for 16 hours, then a saturated $NH_4Cl$ solution was added and the mixture was filtered over celite. $H_2O$ was added to the filtrate and the organic layer was separated, dried ($Na_2SO_4$), filtered off. The solvent was evaporated and the residue was purified by short open column chromatography over silica gel (eluent gradient: EtOAc/($CH_3OH$/$NH_3$ saturated) 97.5/2.5, 95/5, 90/10). The product fractions were collected and the solvent was evaporated. The residue was precipitated from $CH_3CN$, then the resulting solids were filtered off and dried. Yield: 0.197 g of final compound 21 (5%; (3α, 3aα) racemic mixture)).

EXAMPLE B4

Preparation of Final Compound 58

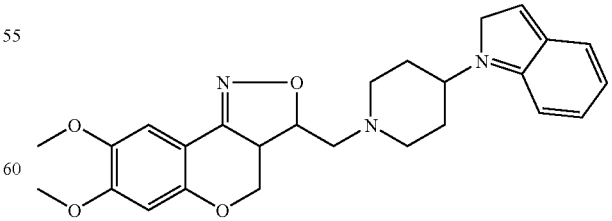

A mixture of an intermediate compound 5 (prepared according to A3) (0.00057 mol), 1-piperidin-4-yl-2H-indole (0.00029 mol) and PS—$NaB(OAc)_2H$ (0.001137 mol) in THF/HOAc 5% (3 ml) and N,N-dimethylformamide (3 ml)

was stirred at room temperature for 16 hours and then the reaction mixture was filtered. PS-p-toluensulfonic acid (0.001137 mol) was added to the filtrate and the resulting mixture was stirred at room temperature for 16 hours. The solvent was evaporated and the resin was washed with DMF, with $CH_2Cl_2$, with $CH_3OH$, with $CH_2Cl_2$ and with dimethyl ether. A saturated $CH_3OH/NH_3$ solution was added to the resin and the mixture was stirred at room temperature for 16 hours, then filtered off and the filtrate was evaporated. The residue was purified by short open column chromatography over silica gel (eluent: EtOAc 100%). The product fractions were collected and the solvent was evaporated. The residue was precipitated from $CH_3CN/DIPE$, the resulting precipitate was collected and dried. Yield: 0.0076 g of final compound 58 (6%; (3α, 3aα) racemic mixture)).

EXAMPLE B5

Preparation of Final Compound 31

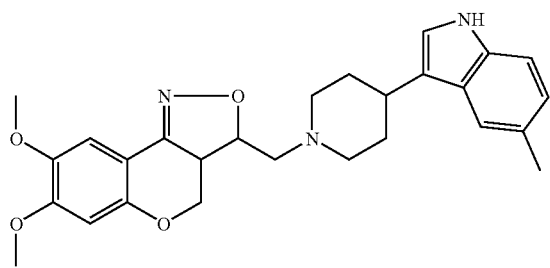

PS—$NaBH_3CN$ (0.0014 mol) was added to a solution of intermediate compound 5 (prepared according to A3) (0.00057 mol) and 5-methyl-3-(4-piperidinyl)-1H-indole* (q.s.) in THF/AcOH (q.s.) was stirred at room temperature for 20 hours. The solution was filtered and the filtrate was incubated with PS-isocyanate (0.0013 mol) and PS—$CH_2N^{(+)}$$(CH_3)_3OH^{(-)}$ (0.0013 mol) overnight at room temperature. The reaction mixture was filtered and the filtrate was evaporated. The residue was purified by short open column chromatography; the product fractions were collected and the solvent was evaporated. The residue was triturated under EtOAc/DIPE (10/1), filtered off and dried. Yield: 0.023 g of final compound 31 (9%, (3αx, 3aα) racemic mixture.

EXAMPLE B6 a) Preparation of Final Compound 33

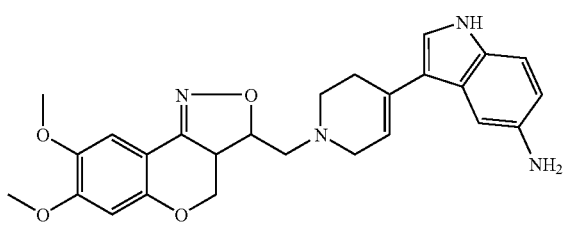

A mixture of intermediate compound 19 (prepared according to A7) (0.010 mol) and trifluoro acetic acid (10 ml) in $CH_2Cl_2$ (90 ml) was stirred at room temperature for 3 hours and then the reaction mixture was alkalised with a 10% aqueous NaOH solution. The organic layer was separated, dried ($Na_2SO_4$), filtered off and the solvent was evaporated. The residue was purified by short open column chromatography over silica gel (eluent: EtOAc 100%). The product fractions were collected and the solvent was evaporated. The residue was precipitated from $CH_3CN/DIPE$, the resulting precipitate was filtered off and dried. Yield: 2.6 g of final compound 33 (45%; (3α, 3aα) racemic mixture)).

b) Preparation of Final Compound 40

A mixture of final compound 33 (prepared according to B6.a) (0.00013 mol), acetylchloride (0.000326 mol) and $Et_3N$ (0.000326 mol) in $CH_2Cl_2$ (5 ml) was stirred at room temperature for 16 hours, PS-trisamine (0.000815 mol) was added and the reaction mixture was shaken at room temperature for 16 hours. The mixture was filtered and the filtrate was evaporated. The residue was purified in a manifold (vacuum) using a Sep-Pak silica gel cartridge (5 g) (eluent gradient: EtOAc/($CH_3OH/NH_3$) 100/0, 97.5/2.5). The product fractions were collected and the solvent was evaporated. The residue was precipitated from $CH_3CN/DIPE$, then the resulting solids were filtered off and dried. Yield: 0.0173 g of final compound 40 (27%; (3α, 3aα) racemic mixture)).

c) Preparation of Final Compound 37

A mixture of final compound 33 (prepared according to B6.a) (0.00013 mol) and ethyl isocyanate (0.000162 mol) in N,N-dimethylformamide (5 ml) was stirred at room temperature for 16 hours, then PS-Trisamine (0.000488 mol) was added and the reaction mixture was stirred for 16 hours. The mixture was filtered off and the filtrate was evaporated. The residue was purified in a manifold (vacuum) using a Sep-Pak silica cartridge (5 g) (eluent: EtOAc 100%). The product fractions were collected and the solvent was evaporated. The residue was precipitated; the resulting precipitate was collected and dried. Yield: 0.0042 g of final compound 37 (6%; (3α, 3aα) racemic mixture)).

EXAMPLE B7

Preparation of Final Compound 34

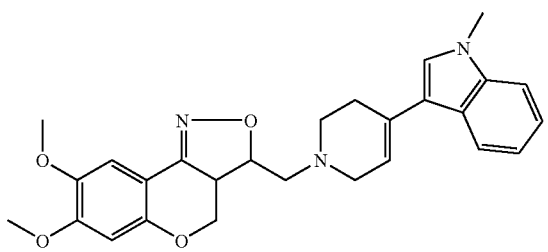

A mixture of final compound 14 (prepared according to B1) (0.00032 mol), dimethylester carbonic acid (0.00095 mol) and $K_2CO_3$ (0.00057 mol) in N,N-dimethylformamide (14 ml) was irradiated with microwaves at 190° C. for 15 minutes, then the reaction mixture was washed with water and extracted with $CH_2Cl_2$. The organic layer was separated, dried ($Na_2SO_4$), filtered off and the solvent was evaporated. The residue was purified in a manifold (vacuum) using a Sep-Pak silica gel cartridge (10 g) (eluent: $CH_2Cl_2/(CH_3OH/NH_3)$ 98/2). The product fractions were collected and the solvent was evaporated. The residue (0.071 g) was further purified by column chromatography on Chromatotron (eluent gradient: $CH_2Cl_2/CH_3OH$ 100/0, 99.5/0.5, 99/1). The product fractions were collected and the solvent was evaporated. The residue was precipitated in DIPE and the resulting solids were collected. Yield: 0.0181 g of final compound 34 (B-(3α, 3aα)).

EXAMPLE B8

Preparation of Final Compound 8

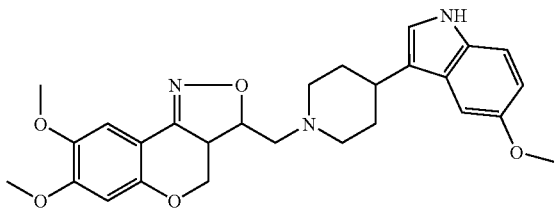

Final compound 7 (prepared according to B1) (0.21 mmol) in EtOAc/EtOH 1:1 (20 ml) was hydrogenated for 3 hours at 70 psi and 50° C. with Pd/C 10% (catalyic quantity) as a catalyst. After uptake of $H_2$ (1 eq), the catalyst was filtered off and the solvent was evaporated. The residue was purified by short open column chromatography over silica gel (eluent: $CH_2C_2/(MeOH/NH_3)$ 98:2). The desired fractions were collected and the solvent was evaporated. Yield: 0.047 g of final compound 8 (47%, (3α, 3aα) racemic mixture).

EXAMPLE B9 a) Preparation of Final Compound 48

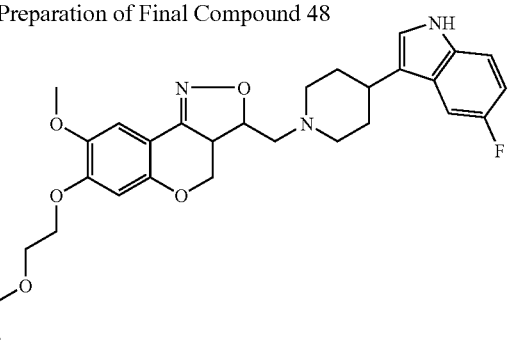

$K_2CO_3$ (0.0018 mol) and 2-bromoethyl acetate (0.0013 mol) were added to a mixture of final compound 65 (prepared according to B1) (0.00089 mol) in DMF (q.s.) and the reaction mixture was stirred at room temperature for 24 hours, then the mixture was partitioned between water and $CH_2Cl_2$. The organic layer was dried ($Na_2SO_4$), filtered off and the solvent was evaporated dry. The residue was purified by column chromatography (short type) over silica gel (eluent: $CH_2Cl_2/(CH_3OH/NH_3)$ 98/2). The product fractions were collected and the solvent was evaporated. Yield: 0.340 g of final compound 48 (63%; (3α, 3aα) racemic mixture).

b) Preparation of Final Compound 47

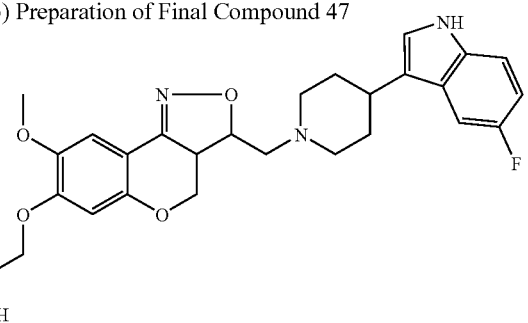

A mixture of LiOH (0.00072 mol) in $H_2O$ (1 ml) was added portionwise at room temperature to a solution of final compound 48 (prepared according to B9.a) (0.00060 mol) in dioxane (6 ml) and then the reaction mixture was stirred for 2 hours at 80° C. The mixture was treated with a saturated. $NH_4Cl$ solution and extracted with EtOAc. The organic layer was separated, dried ($Na_2SO_4$), filtered off and the solvent was evaporated. The residue was purified by short open column chromatography (eluent gradient: $CH_2Cl_2/(CH_3OH/NH_3)$ 99/1, 98/2). The product fractions were collected and the solvent was evaporated. The residue was triturated under $CH_3CN$ and the resulting residue was collected, then purified by reversed phase high-performance liquid chromatography. The product fractions were collected and the solvent was evaporated. Yield: 0.0186 g of final compound 47 (6%; (3α, 3aα) racemic mixture)).

EXAMPLE B10 a. Preparation of Final Compound 66

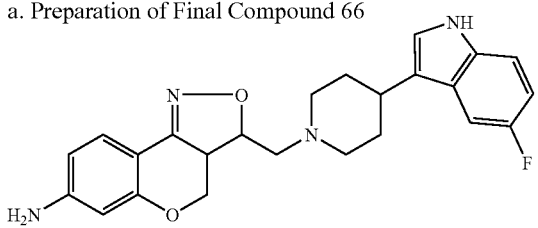

To a solution of intermediate compound 20 (prepared according to A8) (0.21 g, 0.58 mmol) in CH$_2$Cl$_2$ (90 ml) TFA was added (10 ml). The mixture was stirred at room temperature for 16 hours and then Na$_2$CO$_3$ (aqueous saturated solution) was added until pH=8. The organic layer was separated, dried over Na$_2$SO$_4$, filtered and evaporated. The residue was purified by short open column chromatography over silica gel (eluent gradient CH$_2$C$_2$/(MeOH/NH$_3$ sat) 98/2 and 97/3). Desired fractions were collected and evaporated and the residue precipitated from CH$_3$CN/DIPE. Yield: 0.059 g of final compound 66 (34%, (3α, 3aα) racemic mixture)).

b. Preparation of Final Compound 46

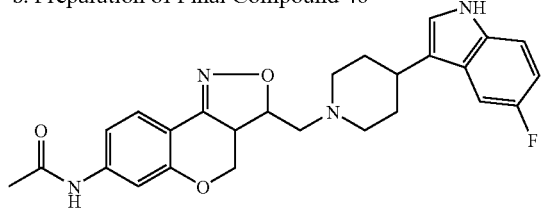

To a solution of final compound 66 (54 mg, 0.13 mmol) in CH$_2$Cl$_2$ (2.5 ml) pyridine (20 ml, 0.26 mmol), acetic anhydride (60 ml, 0.64 mmol) and DMAP (cat) were added. The residue was stirred at room temperature for 16 hours and the mixture was co-evaporated with toluene. The residue was purified by short open column chromatography over silica gel (eluent CH$_2$C$_2$/(MeOH/NH$_3$ sat) 98/2). Desired fractions were collected and evaporated and the residue precipitated from Toluene/CH$_2$Cl$_2$. Yield: 22 mg of final compound 46 (37%, (3β, 3aα) racemic mixture).

EXAMPLE B11

Preparation of Final Compound 62

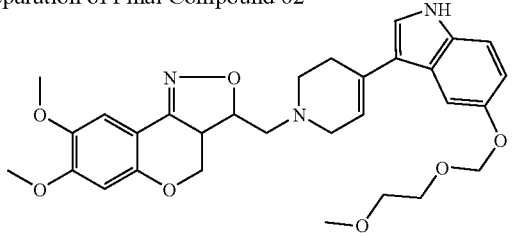

A mixture of final compound 21 (prepared according to B2) (0.00010 mol), 1-(chloromethoxy)-2-methoxyethane (0.00015 mol) and Cs$_2$CO$_3$ (0.00015 mol) in 2-propanone (5 ml) was stirred for 16 hours at room temperature and then the reaction mixture was filtered. The filter residue was purified in a manifold (vac.) using a Sep-Pak silica cartridge (eluent 1: EtOAc 100%; eluent 2: CH$_2$Cl$_2$/(CH$_3$OH/NH$_3$) 98/2, 96/4). The product fractions were collected and the solvent was evaporated. The residue was purified by prep. TLC on Chromatotron (eluent: CH$_2$Cl$_2$/(CH$_3$OH/NH$_3$) 95/5). Finally, the desired product was extracted from the silica gel with CH$_2$Cl$_2$/(CH$_3$OH/satd. NH$_3$) (90/10). Yield: 0.001 g of final compound 62.

EXAMPLE B12

Preparation of Final Compound 22

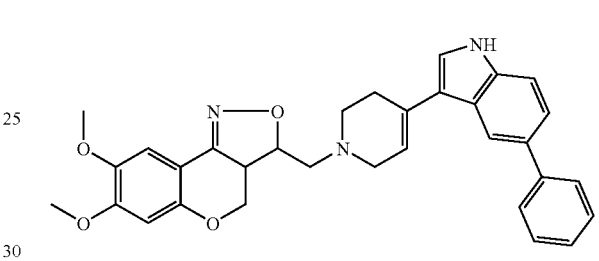

A mixture of final compound 10 (prepared according to B5) (0.00029 mol), phenylboronic acid (0.00031 mol) and catalytic amount of tetrakis(triphenyl phosphine) palladium in a mixture of toluene (10 ml), ethanol (1 ml) and Na$_2$CO$_3$ (1 molar aqueous solution) (1 ml) was stirred at 100° C. in a sealed tube for 16 hours. Then the mixture was filtered through CELITE® and the filtrate was evaporated. The residue was precipitated from CH$_2$Cl$_2$/AcOEt, then the resulting solids were filtered off and dried. Yield: 0.0024 g of final compound 22 (16%; (3α, 3aα) racemic mixture)).

Tables 1 and 2 list the compounds of Formula (I) which were prepared according to one of the above described examples.

TABLE 1

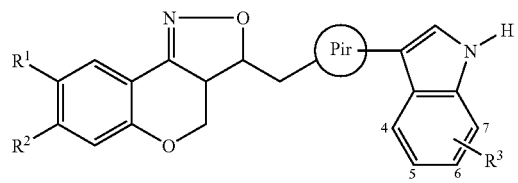

| Co. nr. | Exp. nr. | R$^1$ | R$^2$ | Pir | R$^3$ | Phys. data |
|---|---|---|---|---|---|---|
| 4 | B1 | —OCH$_3$ | —OCH$_3$ | ----NH⟨⟩---- | 5-F | Foam A-(3α, 3aα) |
| 5 | B1 | —OCH$_3$ | —OCH$_3$ | ----NH⟨⟩---- | 5-F | Foam B-(3α, 3aα) |

TABLE 1-continued
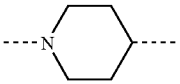
| Co. nr. | Exp. nr. | R¹ | R² | Pir | R³ | Phys. data |
|---|---|---|---|---|---|---|
| 45 | B8 | —OCH₃ | —OCH₃ | 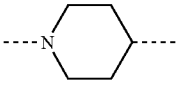 | — | A-(3α, 3aα) Oxalate 190.8° C. |
| 17 | B5 | —OCH₃ | —OCH₃ | 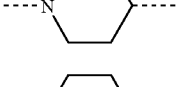 | 4-F | (3α, 3aα) 229.9° C. |
| 2 | B1 | —OCH₃ | —OCH₃ | 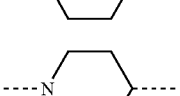 | 5-F | (3α, 3aα) 223.8° C. Decomp. |
| 15 | B1 | —OCH₃ | —OCH₃ | 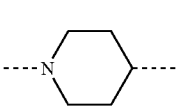 | 5-F | A-(3α, 3aα) Decomp. |
| 11 | B1 | —OCH₃ | —OCH₃ | 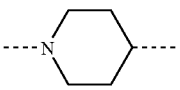 | 5-F | B-(3α, 3aα) Decomp. |
| 29 | B1 | —O—CH₂CH₂—O— | | 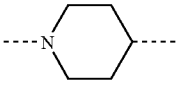 | 5-F | B(3α, 3aα) Foam |
| 65 | B1 | —OCH₃ | —OH | 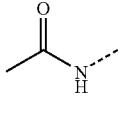 | 5-F | (3α, 3aα) |
| 46 | B10 | H | 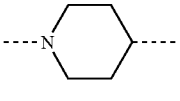 | 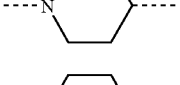 | 5-F | (3α, 3aα) 247.0° C. Decomp. |
| 66 | B10a | H | —NH₂ |  | 5-F | (3α, 3aα) |
| 47 | B9b | —OCH₃ | 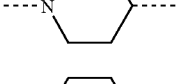 | 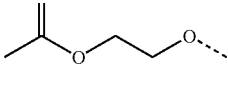 | 5-F | (3α, 3aα) 170.0° C. |
| 48 | B9a | —OCH₃ | 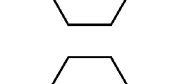 | 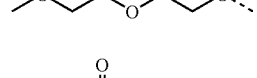 | 5-F | (3α, 3aα) 180.8° C. |
| 49 | B1 | —OCH₃ |  |  | 5-F | (3α, 3aα) 163.3° C. Decomp |
| 50 | B1 | —OCH₃ |  | | 5-F | (3α, 3aα) 145.8° C. |

TABLE 1-continued

[Structure: chromeno-isoxazole with R¹, R² substituents, linked via CH₂ to Pir group, connected to indole with R³ substituent at positions 4,5,6,7]

| Co. nr. | Exp. nr. | R¹ | R² | Pir | R³ | Phys. data |
|---|---|---|---|---|---|---|
| 26 | B5 | —OCH₃ | —OCH₃ | piperidine (N,4-linked) | 6-F | Foam (3α, 3aα) |
| 35 | B1 | —OCH₃ | —OCH₃ | piperidine (N,4-linked) | 6-F | A-(3α, 3aα) Decomp. |
| 36 | B1 | —OCH₃ | —OCH₃ | piperidine (N,4-linked) | 6-F | B-(3α, 3aα) 177.1° C. |
| 51 | B1 | H | pyrrolidinyl-CH₂CH₂-N(CH₃)- | piperidine (N,4-linked) | 6-F | (3α, 3aα) 194.9° C. |
| 52 | B1 | H | morpholinyl-CH₂- | piperidine (N,4-linked) | 6-F | Foam (3α, 3aα) |
| 30 | B5 | —OCH₃ | —OCH₃ | piperidine (N,4-linked) | 7-F | (3α, 3aα) 248.3° C. Decomp. |
| 32 | B5 | —OCH₃ | —OCH₃ | piperidine (N,4-linked) | 5-Cl | Foam (3α, 3aα) |
| 53 | B5 | —OCH₃ | —OCH₃ | piperidine (N,4-linked) | 5-Br | (3α, 3aα) 203.6° C. Decomp |
| 54 | B2 | —OCH₃ | —OCH₃ | piperidine (N,4-linked) | 5-OH | (3α, 3aα) >300° C. |
| 8 | B1 | —OCH₃ | —OCH₃ | piperidine (N,4-linked) | 5-OCH₃ | (3α, 3aα) 202.6° C. Decomp. |
| 20 | B6 | —OCH₃ | —OCH₃ | piperidine (N,4-linked) | 5-NH₂ | (3α, 3aα) 209.6° C. |
| 24 | B5 | —OCH₃ | —OCH₃ | piperidine (N,4-linked) | 5-CN | (3α, 3aα) Decomp. |
| 31 | B5 | —OCH₃ | —OCH₃ | piperidine (N,4-linked) | 5-CH₃ | Foam (3α, 3aα) |

TABLE 1-continued

| Co. nr. | Exp. nr. | R¹ | R² | Pir | R³ | Phys. data |
|---|---|---|---|---|---|---|
| 6 | B1 | —OCH$_3$ | —OCH$_3$ | tetrahydropyridine (N-linked, 4-linked) | — | A-(3α, 3aα) 160.2° C. |
| 14 | B1 | —OCH$_3$ | —OCH$_3$ | tetrahydropyridine | — | B-(3α, 3aα) Decomp. |
| 9 | B1 | —OCH$_3$ | —OCH$_3$ | tetrahydropyridine | 4-F | (3α, 3aα) Decomp. |
| 13 | B1 | —OCH$_3$ | —OCH$_3$ | tetrahydropyridine | 4-F | B-(3α, 3aα) 205.4° C. |
| 16 | A1 | —OCH$_3$ | —OCH$_3$ | tetrahydropyridine | 4-F | A-(3α, 3aα) 222.4° C. |
| 1 | B1 | —OCH$_3$ | —OCH$_3$ | tetrahydropyridine | 5-F | (3α, 3aα) 222.9° C. |
| 3 | B1 | —OCH$_3$ | —OCH$_3$ | tetrahydropyridine | 5-F | A-(3α, 3aα) 202.8° C. |
| 12 | B1 | —OCH$_3$ | —OCH$_3$ | tetrahydropyridine | 5-F | B-(3α, 3aα) 224.4° C. Decomp. |
| 28 | B1 | —O—CH$_2$CH$_2$—O— | | tetrahydropyridine | 5-F | B-(3α, 3aα) Foam |
| 61 | B10 | H | —NH$_2$ | tetrahydropyridine | 5-F | (3α, 3aα) 221.9° C. |
| 55 | B1 | H | morpholin-4-yl | tetrahydropyridine | 5-F | (3α, 3aα) 238.5° C. |
| 56 | B1 | H | pyrrolidin-1-yl-CH$_2$CH$_2$—NH— | tetrahydropyridine | 5-F | (3α, 3aα) 213.0° C. Decomp. |
| 63 | B1 | —OCH$_3$ | —O—CH$_2$—O—CH$_2$CH$_2$—O—CH$_3$ | tetrahydropyridine | 5-F | (3α, 3aα) 180.2° C. |

TABLE 1-continued

| Co. nr. | Exp. nr. | R¹ | R² | Pir | R³ | Phys. data |
|---|---|---|---|---|---|---|
| 27 | B5 | —OCH₃ | —OCH₃ | (1,2,3,6-tetrahydropyridine) | 6-F | Foam (3α, 3aα) |
| 25 | B5 | —OCH₃ | —OCH₃ | (1,2,3,6-tetrahydropyridine) | 5-Cl | (3α, 3aα) Decomp. |
| 10 | B5 | —OCH₃ | —OCH₃ | (1,2,3,6-tetrahydropyridine) | 5-Br | (3α, 3aα) Decomp. |
| 7 | B1 | —OCH₃ | —OCH₃ | (1,2,3,6-tetrahydropyridine) | 5-OCH₃ | Foam (3α, 3aα) |
| 18 | B5 | —OCH₃ | —OCH₃ | (1,2,3,6-tetrahydropyridine) | 5-CH₃ | Foam (3α, 3aα) |
| 19 | B3 | —OCH₃ | —OCH₃ | (1,2,3,6-tetrahydropyridine) | 5-NO₂ | (3α, 3aα) Decomp. |
| 21 | B2 | —OCH₃ | —OCH₃ | (1,2,3,6-tetrahydropyridine) | 5-OH | Foam (3α, 3aα) |
| 62 | B11 | —OCH₃ | —OCH₃ | (1,2,3,6-tetrahydropyridine) | —O—CH₂—O—CH₂CH₂—O—CH₃ | Foam (3α, 3aα) |
| 22 | B12 | —OCH₃ | —OCH₃ | (1,2,3,6-tetrahydropyridine) | 5-phenyl | (3α, 3aα) 154.8° C. |
| 23 | B5 | —OCH₃ | —OCH₃ | (1,2,3,6-tetrahydropyridine) | 5-CN | (3α, 3aα) 229.8° C. Decomp. |
| 33 | B6a | —OCH₃ | —OCH₃ | (1,2,3,6-tetrahydropyridine) | 5-NH₂ | (3α, 3aα) Trifluoroacetate 209.1° C. Decomp. |
| 37 | B6c | —OCH₃ | —OCH₃ | (1,2,3,6-tetrahydropyridine) | 5-NH-C(=O)-NH-ethyl | Foam (3α, 3aα) |
| 38 | B6c | —OCH₃ | —OCH₃ | (1,2,3,6-tetrahydropyridine) | 5-NH-C(=O)-NH-phenyl | (3α, 3aα) 224.2° C. Decomp. |

TABLE 1-continued
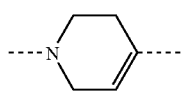
| Co. nr. | Exp. nr. | R$^1$ | R$^2$ | Pir | R$^3$ | Phys. data |
|---|---|---|---|---|---|---|
| 39 | B6c | —OCH$_3$ | —OCH$_3$ | 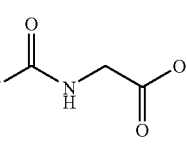 | 5- 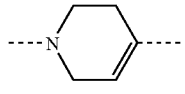 | Foam (3α, 3aα) |
| 40 | B6b | —OCH$_3$ | —OCH$_3$ | 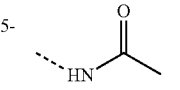 | 5- 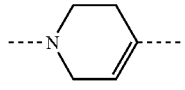 | (3α, 3aα) 223.6° C. Decomp. |
| 41 | B6b | —OCH$_3$ | —OCH$_3$ | 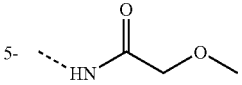 | 5- 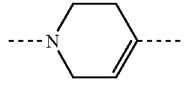 | (3α, 3aα) 208.9° C. |
| 42 | B6b | —OCH$_3$ | —OCH$_3$ | 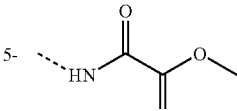 | 5- 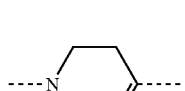 | (3α, 3aα) Decomp. |
| 43 | B6b | —OCH$_3$ | —OCH$_3$ | 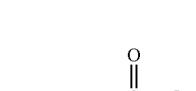 | 5- 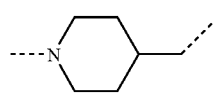 | (3α, 3aα) Trifluoroacetate 228.7° C. |
| 57 | B5 | —OCH$_3$ | —OCH$_3$ | | 5-F | (3α, 3aα) Decomp. |
TABLE 2
| Co. nr. | Exp. nr. | | Physical data |
|---|---|---|---|
| 34 | B7 | 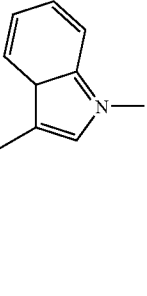 | (3α, 3aα) 170.0° C. |

TABLE 2-continued

| Co. nr. | Exp. nr. | | Physical data |
|---|---|---|---|
| 58 | B4 | 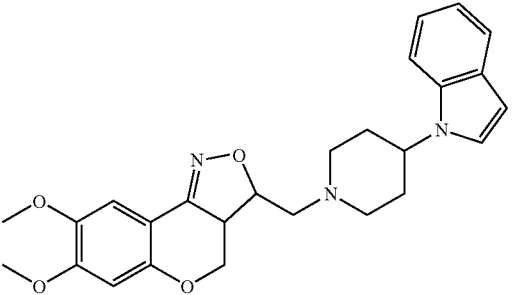 | (3α, 3aα) Decomp. |
| 59 | B4 | 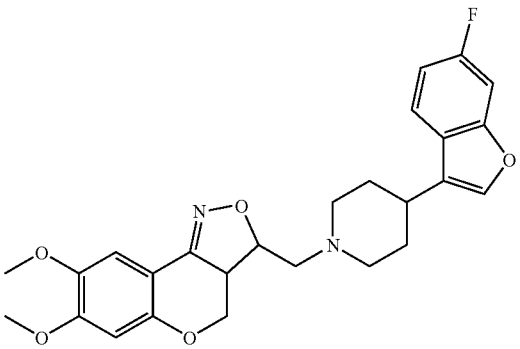 | (3α, 3aα) Decomp. |

C. Pharmacological Example

General

The interaction of the compounds of Formula (I) with dopamine-receptors, h5HT-transporter and h5HT$_{1A}$ receptor was assessed in in vitro radioligand binding experiments. In general, a low concentration of a radioligand with a high binding affinity for a particular receptor or transporter is incubated with a sample of a tissue preparation enriched in a particular receptor or transporter or with a preparation of cells expressing cloned human receptors in a buffered medium. During the incubation, the radioligand binds to the receptor or transporter. When equilibrium of binding is reached, the receptor bound radioactivity is separated from the non-bound radioactivity, and the receptor- or transporter-bound activity is counted. The interaction of the test compounds with the receptor is assessed in competition binding experiments. Various concentrations of the test compound are added to the incubation mixture containing the receptor- or transporter preparation and the radioligand. The test compound in proportion to its binding affinity and its concentration inhibits binding of the radioligand.

EXAMPLE C.1

Binding Experiment for Dopamine D$_2$ and D$_3$ Receptors hD$_2$

Human Dopamine D$_{2L}$ receptor-transfected CHO cells were collected by scraping into ice-cold Tris-HCl buffer (50 mM, pH 7.4). The suspension was centrifuged (23 500×g, 10 min, 4° C.) and pellets stored at −70° C. until required. They were then thawed and briefly homogenised using an Ultra-Turrax T25 homogeniser prior to dilution to an appropriate protein concentration optimised for specific and non-specific binding. [$^3$H]Spiperone (NEN, specific activity ~70 Ci/mmol) was diluted in Tris-HCl assay buffer containing NaCl, CaCl$_2$, MgCl$_2$, KCl (50, 120, 2, 1, and 5 mM respectively, adjusted to pH 7.7 with HCl) at a concentration of 2 nmol/L. Prepared radioligand (50 µl) was then incubated (30 min, 37° C.) with membrane preparations pre-diluted to an appropriate protein concentration (400 µl), and with 50 µl of either the 10% DMSO control, Butaclamol ($10^{-6}$ mol/L final concentration), or compound of interest. Membrane-bound activity was detected by filtration through a Packard Filtermate harvester onto Unifilterplates, washing with ice-cold Tris-HCl buffer (50 mM; pH8.0; 3×4 ml). Filters were allowed to dry before adding scintillation fluid and counting in a Topcount scintillation counter. % Specific bound and competition binding curves were calculated using S-Plus software (Insightful).

hD$_3$

Human Dopamine D$_3$ receptor-transfected CHO cells were collected by scraping into ice-cold Tris-HCl buffer (50 mM, pH 7.4). The suspension was centrifuged (23 500×g, 10 min, 4° C.) and pellets stored at −70° C. until required. They were then thawed and briefly homogenised using an Ultra-Turrax T25 homogeniser prior to dilution to an appropriate protein concentration optimised for specific and non-specific binding. [$^{125}$I]Iodosulpride (Amersham, specific activity 2000 Ci/mmol) was diluted in Tris-HCl assay buffer containing NaCl, CaCl$_2$, MgCl$_2$, KCl and BSA (50, 120, 2, 1, 5 mM, 0.1% respectively, adjusted to pH 7.7 with HCl) at a concentration of 2 nmol/L. Prepared radioligand (20 µl) was incubated (60 min, RT) and with 20 µl of either the 10% DMSO control, Risperidone ($10^{-6}$ mol/L final concentration), or compound of interest, then with membrane preparations (80

μl). Overnight incubation followed after addition of WGA-coated PVT SPA beads (250 μl; Amersham) and membrane-bound counts measured in a Wallac Microbeta. % Specific bound and competition binding curves were calculated using S-Plus software (Insightful).

EXAMPLE C.2

Binding Experiment for 5-HT Transporter

Frozen human 5HT transporter-transfected HEK cells (Perkin Elmer, Brussels) were thawed and briefly homogenised using an Ultra-Turrax T25 homogeniser prior to dilution to an appropriate protein concentration optimised for specific and non-specific binding. [$^3$H]Paroxetine (NEN, specific activity 20 Ci/mmol) was diluted in Tris-HCl assay buffer containing NaCl and KCl (50 mM, 120 mM and 5 mM, respectively; pH 7.4) at a concentration of 5 nmol/L. Prepared radioligand (25 μl) was then incubated (60 min, 25° C.) with membrane preparations (200 μl) and with 25 μl of either 10% DMSO control, Inipramine ($10^{-6}$ mol/L final concentration), or compound of interest. Membrane-bound activity was detected by filtration through a Packard Filtermate harvester onto Unifilterplates pre-soaked in 0.1% PEI, washing with ice-cold assay buffer (3×4 ml). Filters were dried prior to addition of scintillation fluid and then counting in a Topcount scintillation counter. % Specific bound and competition binding curves were calculated using S-Plus software (Insightful).

EXAMPLE C.2

Binding Experiment for 5-HT$_{1A}$ Receptor

Human 5HT$_{1A}$ receptor-transfected L929 cells were collected by scraping into ice-cold Tris-HCl buffer (50 mM, pH 7.4). The suspension was centrifuged (23 500×g, 10 min, 4° C.) and pellets stored at −70° C. until required. They were then thawed and briefly homogenised using an Ultra-Turrax T25 homogeniser prior to dilution to an appropriate protein concentration optimised for specific and non-specific binding. [$^3$H]80HDPAT (NEN, specific activity 127 Ci/mmol) was diluted in Tris-HCl assay buffer containing CaCl$_2$ (50 mM and 4 mM, respectively; pH 7.7) at a concentration of 5 nmol/L. Prepared radioligand (50 μl) was then incubated (30 min, 37° C.) with membrane preparations from L929 cells stably-transfected with the h5HT$_{1A}$ gene construct (400 μl) and with 50 μl of either the 10% DMSO control, spiroxatrine ($10^{-6}$ mol/L final concentration), or compound of interest. Membrane-bound activity was detected by filtration through a Packard Filtermate harvester onto Unifilterplates, washing with ice-cold Tris-HCl buffer (3×4 ml), followed by drying. Scintillation fluid was added and membranes were counted in a Topcount scintillation counter. % Specific bound and competition binding curves were calculated using S-Plus software (Insightful).

The data for the compounds tested have been summarized in Table 3.

TABLE 3

Pharmacological data for the compounds according to the invention.

| Co. No. | pIC$_{50}$ | | | |
|---|---|---|---|---|
| | 5HTT | 5-HT$_{1A}$ | D$_2$ | D$_3$ |
| 57 | 8.3 | 6.4 | 6.3 | nd |
| 51 | 8.2 | 7.7 | 7.9 | nd |

TABLE 3-continued

Pharmacological data for the compounds according to the invention.

| Co. No. | pIC$_{50}$ | | | |
|---|---|---|---|---|
| | 5HTT | 5-HT$_{1A}$ | D$_2$ | D$_3$ |
| 56 | 8.1 | 8.1 | 6.8 | nd |
| 12 | 8.0 | 7.6 | 6.5 | 7.3 |
| 28 | 7.8 | 8.6 | 6.3 | 6.2 |
| 4 | 7.8 | 8.6 | 6.1 | 6.7 |
| 1 | 7.8 | 7.5 | 6.4 | 6.9 |
| 13 | 7.7 | 8.7 | 6.2 | 6.8 |
| 26 | 7.6 | 8.2 | 7.9 | 6.7 |
| 17 | 7.6 | 8.2 | 6.9 | 6.3 |
| 27 | 7.6 | 7.2 | 6.9 | 6.4 |
| 63 | 7.6 | 6.0 | 7.9 | nd |
| 55 | 7.5 | 7.8 | 6.3 | nd |
| 14 | 7.5 | 8.3 | 6.8 | 6.5 |
| 9 | 7.5 | 8.2 | 6.1 | 6.6 |
| 2 | 7.4 | 8.8 | 7.2 | 7.2 |
| 24 | 7.4 | 8.7 | 6.4 | 6.9 |
| 32 | 7.4 | 8.5 | 6.8 | 6.6 |
| 23 | 7.4 | 8.2 | 6.1 | 6.8 |
| 21 | 7.4 | 7.9 | 6.2 | 6.8 |
| 3 | 7.4 | 6.8 | 6.0 | 7.0 |
| 52 | 7.4 | 7.5 | 7.5 | nd |
| 35 | 7.3 | 6.4 | 6.9 | nd |
| 46 | 7.3 | nd | 6.5 | nd |
| 54 | 7.2 | nd | 6.4 | nd |
| 5 | 7.2 | >9 | 6.6 | 7.0 |
| 34 | 7.2 | 7.7 | 5.7 | nd |
| 59 | 7.1 | 7.8 | 7.0 | nd |
| 48 | 7.1 | 8.8 | 6.8 | nd |
| 25 | 7.1 | 8.3 | 6.6 | 6.9 |
| 19 | 7.1 | 8.1 | 6.1 | 6.5 |
| 15 | 7.1 | 7.2 | 6.1 | 6.4 |
| 6 | 7.1 | 6.6 | <6 | 6.2 |
| 18 | 7.0 | 8.2 | 6.4 | 6.4 |
| 45 | 6.9 | 7.0 | 6.3 | nd |
| 61 | 6.9 | 7.3 | nd | nd |
| 49 | 6.9 | nd | 6.7 | nd |
| 11 | 6.9 | 8.9 | 7.2 | 7.2 |
| 29 | 6.9 | 8.8 | 6.6 | 6.5 |
| 16 | 6.9 | 7.1 | 6.0 | 6.5 |
| 50 | 6.9 | 8.6 | 6.8 | nd |
| 36 | 6.8 | 8.0 | 7.5 | nd |
| 31 | 6.7 | 8.5 | 6.4 | 6.4 |
| 10 | 6.7 | 8.3 | 6.3 | 6.5 |
| 30 | 6.5 | 7.4 | 6.0 | 6.4 |
| 7 | 6.4 | 8.1 | <6 | <6 |
| 47 | 6.4 | nd | 7.0 | nd |
| 53 | 6.4 | nd | 6.7 | nd |
| 58 | 6.2 | 7.6 | 6.3 | nd |
| 33 | 6.2 | 7.9 | 5.9 | nd |
| 8 | 5.9 | 8.1 | <6 | 6.0 |
| 22 | 5.6 | 7.6 | 5.4 | 5.5 |
| 20 | 5.4 | 7.6 | 6.2 | <6 |
| 42 | <5.5 | 8.2 | <5 | nd |
| 43 | <5 | 8.7 | 6.0 | nd |
| 40 | <5 | 8.5 | <5 | nd |
| 38 | <5 | 8.4 | <5 | nd |
| 41 | <5 | 8.3 | <5 | nd |
| 37 | <5 | 8.1 | <5 | nd |
| 39 | <5 | 7.8 | <5 | nd |
| 62 | <5 | 7.2 | <5 | nd |

(nd = not determined)

D. Composition Examples

"Active ingredient" (a.i.) as used throughout these examples relates to a compound of Formula (I), the pharmaceutically acceptable acid or base addition salts thereof, the stereochemically isomeric forms thereof, the N-oxide form thereof and prodrugs thereof.

EXAMPLE D.1

Oral Drops

500 Grams of the a.i. is dissolved in 0.5 l of 2-hydroxypropanoic acid and 1.5 l of the polyethylene glycol at 60-80° C. After cooling to 30-40° C. there are added 35 l of polyethylene glycol and the mixture is stirred well. Then there is added a solution of 1750 grams of sodium saccharin in 2.5 l of purified water and while stirring there are added 2.5 l of cocoa flavor and polyethylene glycol q.s. To a volume of 50 l, providing an oral drop solution comprising 10 mg/ml of a.i. the resulting solution is filled into suitable containers.

EXAMPLE D.2

Oral Solution

9 Grams of methyl 4-hydroxybenzoate and 1 gram of propyl 4-hydroxybenzoate are dissolved in 4 l of boiling purified water. In 3 l of this solution are dissolved first 10 grams of 2,3-dihydroxybutanedioic acid and thereafter 20 grams of the a.i. the latter solution is combined with the remaining part of the former solution and 12 l 1,2,3-propanetriol and 3 l of sorbitol 70% solution are added thereto. 40 Grams of sodium saccharin are dissolved in 0.5 l of water and 2 ml of raspberry and 2 ml of gooseberry essence are added. The latter solution is combined with the former, water is added q.s. to a volume of 20l providing an oral solution comprising 5 mg of the active ingredient per teaspoonful (5 ml). The resulting solution is filled in suitable containers.

EXAMPLE D.3

Film-Coated Tablets

Preparation of Tablet Core

A mixture of 100 grams of the a.i., 570 grams lactose and 200 grams starch is mixed well and thereafter humidified with a solution of 5 grams sodium dodecyl sulfate and 10 grams polyvinylpyrrolidone in about 200 ml of water. The wet powder mixture is sieved, dried and sieved again. Then there is added 100 grams microcrystalline cellulose and 15 grams hydrogenated vegetable oil. The whole is mixed well and compressed into tablets, giving 10.000 tablets, each containing 10 mg of the active ingredient.

Coating

To a solution of 10 grams methyl cellulose in 75 ml of denaturated ethanol there is added a solution of 5 grams of ethyl cellulose in 150 ml of dichloromethane. Then there are added 75 ml of dichloromethane and 2.5 ml 1,2,3-propanetriol. 10 grams of polyethylene glycol is molten and dissolved in 75 ml of dichloromethane. The latter solution is added to the former and then there are added 2.5 grams of magnesium octadecanoate, 5 grams of polyvinylpyrrolidone and 30 ml of concentrated color suspension and the whole is homogenated. The tablet cores are coated with the thus obtained mixture in a coating apparatus.

EXAMPLE D.4

Injectable Solution 1.8 Grams methyl 4-hydroxybenzoate and 0.2 grams propyl 4-hydroxybenzoate are dissolved in about 0.5 l of boiling water for injection. After cooling to about 50° C. there are added while stirring 4 grams lactic acid, 0.05 grams propylene glycol and 4 grams of the a.i. The solution is cooled to room temperature and supplemented with water for injection q.s. ad 1 l, giving a solution comprising 4 mg/ml of a.i. The solution is sterilized by filtration and filled in sterile containers.

The invention claimed is:
1. A compound according to the general Formula (I)

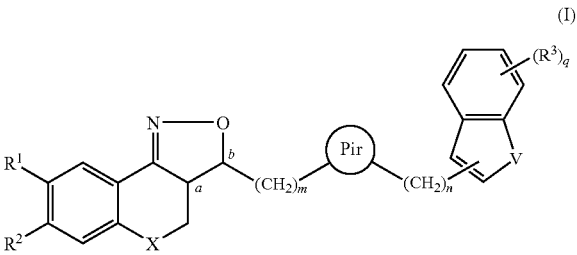

(I)

a pharmaceutically acceptable acid or base addition salt thereof, a stereochemically isomeric form thereof or an N-oxide thereof, wherein:

X is O;

V is O or $NR^5$; wherein $R^5$ is selected from the group of hydrogen and alkyl; or $R^5$ is a covalent bond between the nitrogen and the $(CH_2)_n$ moiety;

$R^1$ and $R^2$ are each, independently from each other, selected from the group of hydrogen; halo; hydroxy; amino; alkyl; cyano; nitro; mono- and di(alkyl)amino; mono- and di(Ar)amino; mono- and di(heteroaryl) amino; mono- and di(alkylcarbonyl)amino; mono- and di(Ar-carbonyl)amino; mono- and di(heteroarylcarbonyl)amino; mono- and di(heteroarylalkyl)amino; alkyloxy; alkylcarbonyloxy; Ar-carbonyloxy; heteroarylcarbonyloxy; alkyloxyalkyloxy; alkyloxyalkyloxyalkyloxy; alkylcarbonyloxyalkyloxy; alkyloxyalkylcarbonyloxyalkyloxy and mono- and di(alkyl)aminocarbonyloxyalkyloxy; or $R^1$ and $R^2$ together may form a bivalent radical of formula —$OCH_2CH_2O$—;

$R^3$ is selected from the group of hydrogen; hydroxy; amino; nitro; cyano; halo; alkyl; alkyloxy; alkyloxyalkyloxy; alkyloxyalkyloxyalkyloxy; Ar; mono- and di(alkyl)aminocarbonylamino; mono- and di(Ar)aminocarbonylamino; mono- and di(alkyloxocarbonylcarbonyl)amino; mono- and di(alkylcarbonyl)amino; mono- and di(alkyloxoalkylcarbonyl) amino and mono- and di(alkylsulphonyl)-amino;

q is an integer equal to zero; 1 or 2;

$(CH_2)_m$ is a covalent bond or a straight hydrocarbon chain of m carbon atoms, m being an integer equal to 1; 2 or 3;

$(CH_2)_n$ is a covalent bond or a straight hydrocarbon chain of n carbon atoms, n being an integer equal to 1; 2; 3 or 4;

Pir is a bivalent radical according to any one of Formula (IIa), (IIb) or (IIc), each radical optionally substituted with p radicals $R^6$, wherein:

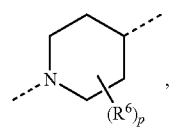
(IIa)

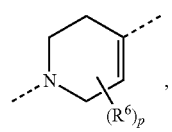
(IIb)

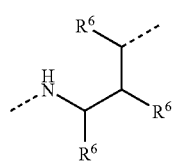
(IIc)

each $R^6$ is independently from each other, selected from the group of hydrogen; hydroxy; amino; nitro; cyano; halo and alkyl;

p is an integer equal to zero; 1 or 2;

Ar is phenyl or naphthyl; each radical optionally substituted with one or more halo, cyano, oxo, hydroxy, alkyl, formyl, alkyloxy or amino radicals;

heteroaryl represents a monocyclic heterocyclic radical selected from the group of azetidinyl; pyrrolidinyl; dioxolyl; imidazolidinyl; pyrrazolidinyl; piperidinyl; homopiperidinyl; dioxyl; morpholinyl; dithianyl; thiomorpholinyl; piperazinyl; imidazolidinyl; tetrahydrofuranyl; 2H-pyrrolyl; pyrrolinyl; imidazolinyl; pyrrazolinyl; pyrrolyl; imidazolyl; pyrazolyl; triazolyl; furanyl; thienyl; oxazolyl; isoxazolyl; thiazolyl; thiadiazolyl; isothiazolyl; pyridinyl; pyrimidinyl; pyrazinyl; pyridazinyl and triazinyl; each heterocyclic radical optionally substituted with one or more radicals selected from the group of alkyl, phenyl, phenyl substituted with alkyl, benzyl, halo, cyano, oxo, hydroxy, formyl, alkyloxy, alkylcarbonyl, tetrahydrofurylcarbonyl and amino; and alkyl represents a straight or branched saturated hydrocarbon radical having from 1 to 6 carbon atoms or a cyclic saturated hydrocarbon radical having from 3 to 6 carbon atoms, each hydrocarbon radical optionally substituted with one or more halo, cyano, oxo, hydroxy, formyl or amino radicals.

2. The compound according to claim 1, the pharmaceutically acceptable acid or base addition salts thereof the stereochemically isomeric forms thereof or the N-oxide thereof, wherein one of $R^1$ and $R^2$ is methoxy.

3. The compound according to claim 1, the pharmaceutically acceptable acid or base addition salts thereof, the stereochemically isomeric forms thereof or the N-oxide thereof, wherein $(CH_2)_m$ is $CH_2$ and $(CH_2)_n$ is a covalent bond or $CH_2$.

4. The compound according to claim 1, the pharmaceutically acceptable acid or base addition salts thereof, the stereochemically isomeric forms thereof or the N-oxide thereof, wherein Pir is an unsubstituted bivalent radical according to any one of Formula (IIa) and (IIb), wherein $R^6$ is hydrogen and p=1.

5. The compound according to claim 1, the pharmaceutically acceptable acid or base addition salts thereof, the stereochemically isomeric forms thereof or the N-oxide thereof, wherein V is $NR^5$, wherein $R^5$ is defined as in Formula (I), $R^3$ is selected from the group of hydrogen, fluoro, chloro, bromo, cyano, methyl, amino, hydroxy, methoxy and nitro and q=1.

6. The compound according to claim 1, the pharmaceutically acceptable acid or base addition salts thereof the stereochemically isomeric forms thereof or the N-oxide thereof, wherein:

$R^1$ and $R^2$ are each, independently from each other, selected from the group of hydrogen; mono- and di(alkylcarbonyl)amino; mono- and di(pyrrolidinylalkyl)amino; alkyloxy; alkyloxyalkyloxyalkyloxy; alkylcarbonyloxyalkyloxy; alkyloxyalkylcarbonyloxyalkyloxy; mono- and di(alkyl)aminocarbonyloxyalkyloxy and morpholinyl; or $R^1$ and $R^2$ together may form a bivalent radical of formula $-OCH_2CH_2O-$;

$R^3$ is selected from the group of hydrogen; hydroxy; amino; nitro; cyano; halo; alkyl; alkyloxy; alkyloxyalkyloxyalkyloxy; Ar; mono- and di(alkyl)aminocarbonylamino; mono- and di(Ar)aminocarbonylamino; mono- and di(alkyloxocarbonylcarbonyl)amino; mono- and di(alkylcarbonyl)amino; mono- and di(alkyloxoalkylcarbonyl)amino and mono- and di(alkylsulphonyl)amino;

q is an integer equal to zero or 1;

$(CH_2)_m$ a straight hydrocarbon chain of m carbon atoms, m being an integer equal to 1;

$(CH_2)_n$ is a covalent bond or a straight hydrocarbon chain of n carbon atoms, n being an integer equal to 1;

Ar is phenyl; and alkyl represents a straight or branched saturated hydrocarbon radical having from 1 to 2 carbon atoms; each radical optionally substituted with a hydroxyl radical.

7. A pharmaceutical composition comprising a pharmaceutically acceptable carrier or diluent and, as active ingredient, a therapeutically effective amount of a compound according to claim 1, a pharmaceutically acceptable acid or base addition salt thereof, a stereochemically isomeric form thereof or an N-oxide thereof.

8. A process for preparing a compound according to claim 1 comprising either a) alkylating a mesylate intermediate of Formula (III) with an intermediate of Formula (IV) in a reaction-inert solvent and in the presence of a suitable base

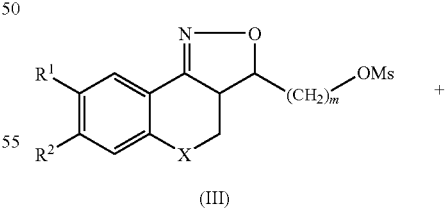
(III)

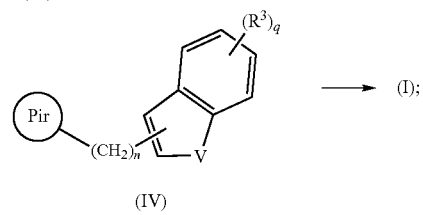
(IV)
$\longrightarrow$ (I);

b) reductively aminating an aldehyde intermediate of Formula (V) with an intermediate of Formula (IV) in a reaction-inert solvent and in the presence of a reducing agent

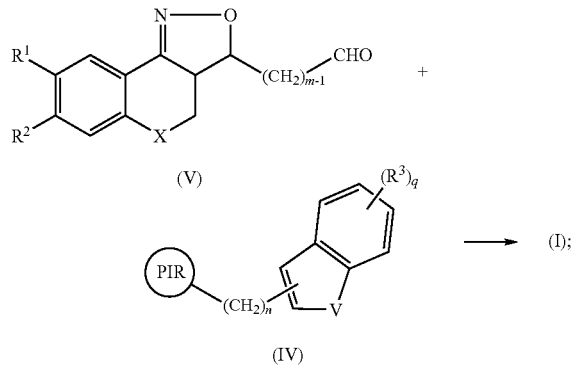

(c) and optionally, converting compounds of Formula (I) into each other following art-known transformations, and further, optionally, converting the compounds of Formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, optionally, preparing stereochemically isomeric forms, N-oxides thereof and quaternary ammonium salts thereof.

9. The compound according to claim 1, the pharmaceutically acceptable acid or base addition salts thereof, the stereochemically isomeric forms thereof or the N-oxide thereof, wherein $R^1$ and $R^2$ are methoxy.

* * * * *

UNITED STATES PATENT AND TRADEMARK OFFICE
CERTIFICATE OF CORRECTION

PATENT NO. : 7,635,696 B2
APPLICATION NO. : 11/791510
DATED : December 22, 2009
INVENTOR(S) : Andrés-Gil et al.

It is certified that error appears in the above-identified patent and that said Letters Patent is hereby corrected as shown below:

In the Specification

Column 21,
Line 37, delete "$CH_2C_2$" and insert -- $CH_2Cl_2$ --.
Line 64, delete "$CH_2C_2$" and insert -- $CH_2Cl_2$ --.

Column 23,
Line 10, delete "$CH_2C_2$" and insert -- $CH_2Cl_2$ --.

Column 27,
Line 65, delete "$CH_2C_2$" and insert -- $CH_2Cl_2$ --.

Column 29,
Line 8, delete "$CH_2C_2$" and insert -- $CH_2Cl_2$ --.
Line 27, delete "$CH_2C_2$" and insert -- $CH_2Cl_2$ --.

Column 32,
Table 1-continued, Co. nr 11, in Phys. data, delete "B-(3α, 3aα), Decomp." and insert -- B-(3α, 3aα), 162.7°C. --.

Column 43,
Line 41, delete "[$^3$H]80HDPAT" and insert -- [$^3$H]8OHDPAT --.

Signed and Sealed this
Twenty-eighth Day of January, 2014

Michelle K. Lee
*Deputy Director of the United States Patent and Trademark Office*